United States Patent
Tumu et al.

(10) Patent No.: US 11,998,770 B2
(45) Date of Patent: Jun. 4, 2024

(54) RESPIRATOR ASSEMBLY AND METHOD OF USING THE SAME

(71) Applicant: HONEYWELL INTERNATIONAL INC., Charlotte, NC (US)

(72) Inventors: Anjaiah Tumu, Charlotte, NC (US); Rahul Ramesh Bhaskarwar, Charlotte, NC (US); Garaga Phani Kumar, Charlotte, NC (US)

(73) Assignee: Honeywell International Inc., Charlotte, NC (US)

( * ) Notice: Subject to any disclaimer, the term of this patent is extended or adjusted under 35 U.S.C. 154(b) by 467 days.

(21) Appl. No.: 17/329,674

(22) Filed: May 25, 2021

(65) Prior Publication Data
US 2021/0379308 A1   Dec. 9, 2021

(30) Foreign Application Priority Data
Jun. 4, 2020   (IN) .............................. 202011023489

(51) Int. Cl.
*A62B 18/00*   (2006.01)
*A61M 16/00*   (2006.01)

(52) U.S. Cl.
CPC ....... *A62B 18/006* (2013.01); *A61M 16/0066* (2013.01); *A61M 16/024* (2017.08);
(Continued)

(58) Field of Classification Search
CPC ..... A62B 18/006; A62B 18/045; A62B 27/00; A61M 16/0057; A61M 16/0066; A61M 16/0069; A61M 16/024; A61M 2205/3331; A61M 2205/3334; A61M 2205/3365; A61M 2205/52; A42B 3/286
See application file for complete search history.

(56) References Cited

U.S. PATENT DOCUMENTS 8,931,482 B2   1/2015   Hansmann et al.
9,119,979 B2   9/2015   Curran et al.
(Continued)

OTHER PUBLICATIONS

Extended European Search Report issued in European Application No. 21175472.6 dated Sep. 22, 2021, 6 pages.
(Continued)

*Primary Examiner* — Joseph D. Boecker
(74) *Attorney, Agent, or Firm* — Alston & Bird LLP

(57) ABSTRACT

Various embodiments are directed to a method for operating a blower so as to generate an at least substantially consistent output flowrate comprising programmatically determining an optimized motor speed based at least in part on blower motor data and a blower characterization curve, wherein the blower characterization curve defines a correlation between motor speed and motor voltage of a blower motor configured to generate a desired respirator output flowrate; and programmatically adjusting a motor voltage based at least in part on a comparison of measured motor speed data to the optimized motor speed, wherein the blower characterization curve is defined by one or more blower characterization equations derived based at least in part on a plurality of motor output calibration points. Various embodiments are directed to a respirator apparatus configured to generate an at least substantially consistent respirator output airflow.

20 Claims, 8 Drawing Sheets

(52) U.S. Cl.
CPC ............ *A61M 2205/3331* (2013.01); *A61M 2205/3334* (2013.01); *A61M 2205/3365* (2013.01); *A61M 2205/3368* (2013.01); *A61M 2205/52* (2013.01)

(56) References Cited

U.S. PATENT DOCUMENTS

| | | | | |
|---|---|---|---|---|
| 2008/0127979 | A1* | 6/2008 | Becker | A62B 18/006 128/205.27 |
| 2012/0017906 | A1* | 1/2012 | Hansmann | A62B 7/10 128/205.12 |
| 2012/0138051 | A1* | 6/2012 | Curran | F04D 27/004 128/201.25 |
| 2012/0260918 | A1* | 10/2012 | Sayers | A62B 7/10 128/204.21 |
| 2019/0126077 | A1 | 5/2019 | Kilmer et al. | |

OTHER PUBLICATIONS

EP Office Action Mailed on Jan. 29, 2024 for EP Application No. 21175472, 5 page(s).

\* cited by examiner

RESPIRATOR ASSEMBLY AND METHOD OF USING THE SAME

CROSS-REFERENCE TO RELATED APPLICATIONS

This application claims priority pursuant to 35 U.S.C. 119(a) of India Patent Application No. 202011023489, filed Jun. 4, 2020, which application is incorporated herein by reference in its entirety.

FIELD OF THE INVENTION

Various embodiments described herein relate generally to a respirator apparatus and method of using the same. In particular, various embodiments are directed to respirators configured for delivering to a user a consistent flow of breathable air to a user.

BACKGROUND

Industrial and commercial applications may use respirators comprising blowers to provide a powered flow of air. Through applied effort, ingenuity, and innovation, Applicant has solved problems relating to respirators by developing solutions embodied in the present disclosure, which are described in detail below.

BRIEF SUMMARY

Various embodiments are directed to a respirator assembly and method of using the same. In various embodiments, an exemplary method for operating a blower so as to generate an at least substantially consistent output flowrate may comprise programmatically determining an optimized motor speed based at least in part on blower motor data and a blower characterization curve, wherein the blower characterization curve defines a correlation between motor speed and motor voltage of a blower motor configured to generate a desired respirator output flowrate; and programmatically adjusting a motor voltage based at least in part on a comparison of measured motor speed data to the optimized motor speed; wherein the blower characterization curve is defined by one or more blower characterization equations derived based at least in part on a plurality of motor output calibration points.

In various embodiments, the optimized motor speed may comprise the motor speed required for the blower motor to generate the desired respirator output flowrate given the measured motor voltage data; and at least one of the motor output calibration points may correspond to a respective calibrated operating state defined by a blower production output and a calibrated blower motor configuration wherein the blower motor producing the blower production output and operating at a calibrated motor speed and a calibrated motor voltage is configured to generate the desired respirator output flowrate. In various embodiments, the plurality of motor output calibration points may comprise at least three motor output calibration points such that the blower characterization curve comprises a plurality of blower motor operational ranges, each blower motor operational range being defined by adjacent motor output calibration points of the plurality of motor output calibration points, and wherein each of the one or more blower characterization equations corresponds to a respective blower motor operational range such that the blower characterization curve is defined by a plurality of blower characterization equations. In certain embodiments, the method may further comprise generating the blower motor data comprising the measured motor speed data and measured motor voltage data, wherein programmatically determining the optimized motor speed comprises identifying a measured blower motor operational range based at least in part on the measured motor voltage data and identifying the blower characterization equation corresponding to measured blower motor operational range.

In various embodiments, the one or more blower characterization equations may comprise a derived correlation between the motor speed and the motor voltage of the blower motor configured to generate the desired respirator output flowrate, wherein the derived correlation is based at least in part on the calibrated motor data corresponding to the plurality of motor output calibration points. In various embodiments, the derived correlation may comprise an at least substantially linear correlation. In various embodiments, the method may further comprise adjusting the measured motor speed based at least in part on measured ambient temperature data. In various embodiments, the method may further comprise adjusting the measured motor speed based at least in part on measured ambient pressure data. In certain embodiments, the method may further comprise further comprising adjusting the measured motor speed based at least in part on measured ambient temperature data.

In various embodiments, the method may further comprise identifying the plurality of motor output calibration points based at least in part on a maximum blower production output of the blower motor. In various embodiments, programmatically adjusting the motor voltage may comprise adjusting a pulse width modulation configuration of the blower motor such that the motor speed of the blower motor is adjusted so as to maintain the respirator output flowrate that is at least substantially consistent with the desired respirator output flowrate. In various embodiments, the method may further comprise programmatically determining an optimized motor current based at least in part on the blower motor data and a second blower characterization curve, wherein the second blower characterization curve defines a correlation between motor current and motor voltage of the blower motor configured to generate the desired respirator output flowrate, wherein the optimized motor current comprises a motor current required for the blower motor to generate the desired respirator output flowrate given measured motor voltage data; and programmatically adjusting a motor voltage based at least in part on a comparison of the measured motor current data to the optimized motor current. In various embodiments, the comparison of the measured motor speed data to the optimized motor speed may comprise comparing the measured motor speed to the optimized motor speed in order to determine whether the measured motor speed falls within an acceptable measured motor speed tolerance range defined in part by the optimized motor speed and comprising a range of motor speed values configured to cause the blower motor operating at the measured motor voltage to generate a respirator output flowrate that is at least substantially consistent with the desired respirator output flowrate.

Various embodiments are directed to a respirator apparatus configured to generate an at least substantially consistent respirator output airflow, the respirator apparatus comprising: a blower assembly comprising a blower motor configured to control a blower so as to drive a volume of air through a respirator air outlet at a respirator output flowrate; and a controller comprising at least one processor, and at least one non-transitory memory comprising instructions that, with the at least one processor, cause the controller to:

programmatically determine an optimized motor speed based at least in part on blower motor data and a blower characterization curve, wherein the blower characterization curve defines a correlation between motor speed and motor voltage of a blower motor configured to generate a desired respirator output flowrate; and programmatically adjust a motor voltage based at least in part on a comparison of the measured motor speed data to the optimized motor speed; wherein the blower characterization curve is defined by one or more blower characterization equations derived based at least in part on a plurality of motor output calibration points.

In various embodiments, the optimized motor speed may comprise the motor speed required for the blower motor to generate the desired respirator output flowrate given the measured motor voltage data; and wherein at least one of the motor output calibration points corresponds to a respective calibrated operating state defined by a blower production output and a calibrated blower motor configuration wherein the blower motor producing the blower production output and operating at a calibrated motor speed and a calibrated motor voltage is configured to generate the desired respirator output flowrate. In various embodiments, the plurality of motor output calibration points may comprise at least three motor output calibration points such that the blower characterization curve comprises a plurality of blower motor operational ranges, each blower motor operational range being defined by adjacent motor output calibration points of the plurality of motor output calibration points, and wherein each of the one or more blower characterization equations corresponds to a respective blower motor operational range such that the blower characterization curve is defined by a plurality of blower characterization equations. In certain embodiments, the at least one non-transitory memory may further comprise instructions that, with the at least one processor, cause the apparatus to generate the blower motor data comprising the measured motor speed data and measured motor voltage data, wherein programmatically determining the optimized motor speed comprises identifying a measured blower motor operational range based at least in part on the measured motor voltage data and identifying the blower characterization equation corresponding to measured blower motor operational range.

In various embodiments, the one or more blower characterization equations may comprise a derived correlation between the motor speed and the motor voltage of the blower motor configured to generate the desired respirator output flowrate, wherein the derived correlation is based at least in part on the calibrated motor data corresponding to the plurality of motor output calibration points. In various embodiments, the at least one non-transitory memory may further comprise instructions that, with the at least one processor, cause the apparatus to adjust the measured motor speed based at least in part on measured ambient temperature data. In various embodiments, the at least one non-transitory memory may further comprise instructions that, with the at least one processor, cause the apparatus to adjust the measured motor speed based at least in part on measured ambient pressure data.

BRIEF DESCRIPTION OF THE DRAWINGS

Reference will now be made to the accompanying drawings, which are not necessarily drawn to scale, and wherein.

DETAILED DESCRIPTION

Figure 1:
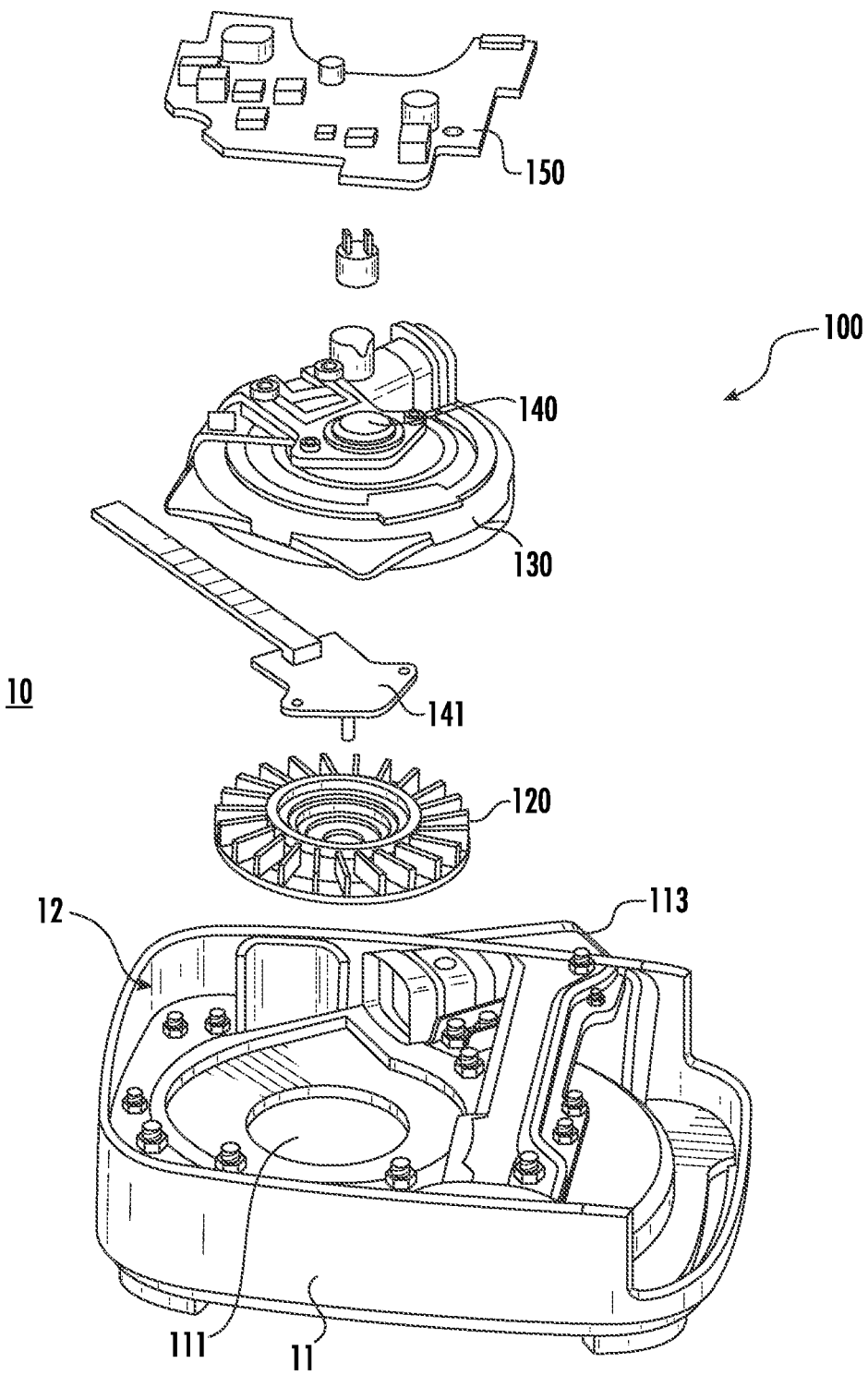
FIG. 1 illustrates an exploded perspective view of various components of an exemplary respirator apparatus in accordance with various embodiments.

The present disclosure more fully describes various embodiments with reference to the accompanying drawings. It should be understood that some, but not all embodiments are shown and described herein. Indeed, the embodiments may take many different forms, and accordingly this disclosure should not be construed as limited to the embodiments set forth herein. Rather, these embodiments are provided so that this disclosure will satisfy applicable legal requirements. Like numbers refer to like elements throughout.

It should be understood at the outset that although illustrative implementations of one or more aspects are illustrated below, the disclosed assemblies, systems, and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents. While values for dimensions of various elements are disclosed, the drawings may not be to scale.

The words "example," or "exemplary," when used herein, are intended to mean "serving as an example, instance, or illustration." Any implementation described herein as an "example" or "exemplary embodiment" is not necessarily preferred or advantageous over other implementations.

Powered air purifying respirators (PAPRs) are used in various applications to provide a user with a constant supply of breathable air in circumstances wherein the air within an ambient in the user's environment is highly contaminated, infectious, polluted, or otherwise unsafe for user consumption. In various industries, an employee working in an environment in which breathing the ambient air of the environment may be hazardous to the user's health may utilize various forms of personal protective equipment (PPE) or breathing apparatuses, such as masks, respirators, ventilators, loose-fitting hoods and/or full-body suits in order to avoid inhaling the potentially hazardous ambient air. Various breathing apparatuses may be bulky and/or immobile, such that a user's mobility during use may be substantially limited. Further, various PPE may not be configured to provide a level of protection sufficient to ensure that a user is provided with breathable air in highly-contaminated and/or dangerous environments. Further still, various PPE may include expensive measurement hardware devices configured to dynamically monitor various operating characteristics of the PPE such that the performance of the PPE may be tracked over time to ensure that the PPE is operating according to one or more desired performance parameters.

In some examples, a PAPR may comprise a self-contained breathing apparatus that utilizes a powered fan system to deliver a consistent flow of breathable air to a user. Often, a PAPR may comprise an in-line filter assembly configured to receive a volume of ambient air passing through the PAPR and purify the air before it is supplied to the user. For example, various PAPRs may comprise a motor-driven blower that may generate a substantially consistent flow of air from the ambient environment along an air flow path so as to deliver a volume of breathable air to a controlled environment within a protective helmet, mask, and or the like, for example, from which a user may breath exclusively breathable air. Blowers may be configured within PAPRs to pull air from the ambient environment and drive the air to the controlled environment at a substantially consistent flow rate. As described above, various PAPRs may utilize expensive measurement hardware, such as, for example, flow sensors and/or differential pressure sensors in order to monitor the output flowrate of the PAPR. For example, based at least in part on the feedback from the flow sensors and/or differential pressure sensors providing the respirator output flowrate, the PAPR may be configured to adjust one or more operating parameters of the blower assembly included therein in order to ensure that the output flowrate readings of the flow sensors and/or differential pressure sensors remain constant. Such a dynamic performance characterization process that utilizes expensive measurement hardware devices can lead to increased manufacturing costs caused by increased part costs, tooling costs, production costs, and operational costs.

Further, various PAPRs may utilize calibration curves defining general relationships between various operating parameters of a blower motor such as, for example, motor speed and motor current to infer the output airflow being generated by the respirator. In various embodiments, the behavior of various blower motor operating parameters of a respirator may be affected by one or more respirator operating conditions (e.g., a respirator having a clogged filter assembly) and/or various ambient environment conditions, such as temperature or altitude. For example, as described herein, the various correlations between the blower motor operating parameters may deviate from their optimized configurations at various blower motor production outputs and/or when the blower motor is subjected to one or more respirator operating conditions and/or variances in ambient environment conditions. As such, various PAPRs configured to monitor the respirator output flowrate using oversimplified blower characterization curves may experience various inaccuracies, for example, caused by deviations in one or more blower motor operating parameter relationships caused by factors realized by the blower motor in practice. Further, blower characterization curves can often be extremely dependent on the physical configuration of the blower defined thereby. In various embodiments, a PAPR configured to produce a consistent respirator output flowrate by monitoring one or more blower motor operational parameters defined by a blower characterization curve that is not calibrated to the particular blower assembly may experience output inaccuracies, as described herein.

Described herein are example respirator assemblies configured to produce an at least substantially consistent output airflow. An exemplary method for operating a blower assembly so as to generate an at least substantially consistent respirator output airflow is described herein. As described herein, the speed of the blower motor may be utilized to represent the respirator output flowrate generated by the blower. For example, the exemplary method described herein may comprise utilizing a blower characterization curve correlating the motor speed of the blower motor to the motor pulse width modulation (PWM) for an exemplary blower configured to produce a desired respirator output flowrate in order to monitor the respirator output flowrate generated by the blower motor. For example, the blower characterization curve may be derived using a plurality of motor output calibration points, as described herein. The motor output calibration points may be identified based at least in part on a maximum blower production output. In order to more accurately characterize the dynamic behavior of the respirator blower assembly (e.g., the blower motor) over a full blower motor operational range, the plurality of motor output calibration points may be identified so as to define one or more blower motor operational ranges, as described herein. As described herein, each motor output calibration point may function as a defined blower motor operating state at which one or more of the blower motor operating parameters are to be defined so as to facilitate an accurate approximation of one or more other blower motor operating parameters. Further, one or more blower characterization equations defining a relationship between various blower motor operating parameters within a blower motor operational range may be derived. For example, in various embodiments, a blower characterization equation may be derived in order to define the relationship between the motor speed and the motor voltage for a blower motor operating within a particular blower motor operational range.

As described herein, a blower characterization equation may be derived for each blower motor operational range, such that the blower characterization curve is defined by a plurality of distinctly derived blower characterization equations corresponding to the particular blower motor operational range corresponding thereto. In such an exemplary configuration, by defining the blower characterization curve based on the motor output calibration points, a single blower characterization curve may be used to accurately define the relationship between, for example, the motor speed, motor current and the motor PWM throughout the full blower motor operational range. Such an exemplary configuration minimizes production time and manufacturing costs associated with integrating a multitude of overlapping blower characterization curves into a single collection of data to be used broadly across a wide array of blower motor operational states. Further, utilizing one or more derived blower characterization equations corresponding to various blower motor operational ranges defined by a plurality of motor output calibration points allows for a more granular analysis of the relationships between the various blower motor operating parameters. Such an exemplary configuration enables the blower characterization equations by which the respirator output flowrate is monitored to be more tailored to the particular behavior of the blower motor within a particular operational range. Further, such an exemplary configuration may result in an increased system accuracy while maintaining a substantially low manufacturing cost.

Further, as described herein, the exemplary method for operating a blower so as to maintain a substantially consistent respirator output flowrate may comprise compensating for both ambient temperature and altitude in order to ensure that the motor speed value utilized to indicate the respirator output flowrate is programmatically adjusted to account for the effect of the ambient environment on the blower assembly. By compensating for the variances in blower motor behavior caused by the ambient environment, an exemplary apparatus and method may further facilitate increased system accuracy while maintaining substantially low product cost and/or manufacturing costs.

In various embodiments, a respirator may be configured to receive a volume of air from an ambient environment, purify the volume of air by removing at least a portion of the contaminant present within the volume of air (e.g., particulate matter, airborne pathogens, and/or the like), and transmit the purified volume of air to a controlled environment adjacent a mouth of a user wearing the respirator such that the user may inhale a volume of purified air. As described herein, in various embodiments, an exemplary respirator may comprise a respirator housing defining a respirator air inlet that is fluidly engaged with an ambient environment and a respirator air outlet that is fluidly engaged with a controlled environment defined by an air-tight an article of personal protective equipment, such as, for example, a facemask, an enclosed hood, and/or the like, that is configured to isolate the controlled environment from the ambient environment. The respirator housing may be configured to receive a volume of air from the ambient environment and may define an air flow path extending between the respirator air inlet and the respirator air outlet such that a volume of air received at the respirator air inlet may travel from the respirator air inlet along the fluid flow path to the respirator air outlet.

In various embodiments, an exemplary respirator may comprise a blower assembly configured to pull a volume of air from the ambient environment into the respirator and facilitate the flow of the received volume of air from the respirator air inlet, along the air flow path, and out of the respirator through the respirator air outlet into the controlled environment. In various embodiments, the blower assembly may define a blower assembly air flow path extending between a blower assembly air inlet and a blower assembly air outlet along which the volume of air received by the blower assembly may travel. In various embodiments, the blower assembly air flow path may define a portion of the respirator air flow path. For example, the blower assembly may be fluidly connected to the respirator air inlet (e.g., either directly or indirectly) such that, in operation, the blower assembly may pull a volume of air from an ambient environment into the respirator air inlet to a blower assembly air inlet. Further, the blower assembly may be further fluidly connected to a respirator air outlet (e.g., either directly or indirectly) such that, the volume of air received at the blower assembly air inlet may be driven out from the blower assembly air outlet to the respirator air outlet to a controlled environment, as described herein. The blower assembly air flow path may define a portion of the respirator air flow path positioned downstream from the blower assembly air inlet and upstream from the blower assembly air outlet.

In various embodiments, an exemplary respirator described herein may further comprise a filter assembly configured to extract various contaminants from within a volume of air received by the respirator from an ambient environment such that the volume of air is at least partially purified prior to being dispensed into a controlled environment, as described herein. In various embodiments, the filter assembly may define at least a portion of the respirator air flow path such that a volume of air traveling from the respirator air inlet and along the air flow path may pass through the filter assembly. For example, the filter assembly may comprise a filter element configured to capture various contaminates such as, for example, particulate matter, airborne bacteria, and/or the like, from the volume of air traveling along the respirator air flow path. In various embodiments, the filter assembly may be positioned upstream from the respirator air outlet such that the contaminants present within the volume of ambient air received by the respirator are extracted prior to the volume of air being dispensed into the controlled environment, thereby minimizing the amount of contaminant within the purified air of the controlled environment.

FIG. 1 illustrates an exploded perspective view of an exemplary respirator apparatus 10 in accordance with various embodiments. As illustrated, the respirator housing 11 may be configured such that at least substantially all of a blower assembly 100 may be disposed within an internal respirator housing portion 12 defined at least in part by one or more sidewalls of the respirator housing. For example, FIG. 1 illustrates an exploded top perspective view and an exploded bottom perspective view, respectively of an exemplary blower assembly 100 arranged relative to a respirator housing 11 in accordance with various embodiments. In various embodiments, a blower assembly 100 may comprise an impeller 120, a scroll cover 130, a blower motor 140, and a printed control board assembly (PCBA) 150.

In various embodiments, the blower assembly 100 may comprise a blower assembly air inlet 111 that is fluidly connected to the respirator air inlet (e.g., either directly or indirectly) such that, in operation, the blower assembly 100 may pull a volume of air into the blower assembly air inlet 111 using an impeller 120. As described herein, the impeller 120 of the blower assembly 100 may define a centrifugal fan component comprising a plurality of radial impeller blades configured to generate airflow within the blower assembly by rotating about a central impeller axis. The blower assembly 100 may be configured such that upon the rotation of the impeller 120, a volume of air may be pulled into the blower assembly air inlet 111, through an impeller intake portion, and pushed in an outward radial direction to a blower assembly air outlet 113. In various embodiments, the rotation of the impeller 120 may cause the volume of air to be pulled into blower assembly air inlet 111 from the ambient environment via the respirator air inlet. In various embodiments, a scroll cover 130 may be configured to at least partially surround the impeller 120 so as direct an air flow generated by the impeller 120 toward a blower assembly outlet 113. For example, the scroll cover 130 may define a scroll cover cavity 132 configured such that at least a portion of the impeller 120 may be arranged therein. In various embodiments, the scroll cover 130 may be configured to at least partially define a blower scroll, which may comprise an internal scroll flow chamber configured to house the impeller 120 and define at least substantially all of the blower assembly air flow path extending between the blower assembly air inlet and the blower assembly air outlet.

In various embodiments, an impeller 120 may be connected to a blower motor 140 configured to drive the rotation of the impeller 120 about the central impeller axis. In various embodiments, the blower motor 140 may comprise a direct current (DC) motor, such as, for example, a brushed DC motor, a brushless DC motor, and/or the like. Alternatively, in various embodiments, the blower motor 140 may comprise an alternating current (AC) motor. A blower motor 140 may comprise, for example, a rotary assembly and a stator configured to translate one or more electrical signals into the physical motion of the impeller 120. For example, in various embodiments, the blower motor 140 may be configured to receive one or more electrical signals from a PCBA 150 (e.g., via an electrical connection elements 141), as described herein. In response, the blower motor 140 may cause at least a portion of the rotary assembly attached thereto (e.g., a rotary shaft) to rotate. In various embodiments, a portion of the impeller 120 may be secured to the rotary assembly such that the rotation of a portion of the rotary assembly may drive the rotational motion of the impeller 120. In various embodiments, the PCBA 150 may comprise a singular printed circuit board including both motor control circuitry configured to electronically communicate with the blower motor 140 so as to facilitate control thereof. Further, in various embodiments, the PCBA 150 may comprise various respirator operation circuitries configured to electronically communicate with various electrical components of the exemplary respirator 10 described herein so as to facilitate operability thereof. In various embodiments, at least a portion of an exemplary controller described in further herein with respect to FIG. 3, may be integrated into the PCBA 150. For example, an exemplary controller may comprise various circuitries defined by the PCBA 150.

As described herein, the impeller 120 may be controlled according to one or more operating parameters of the blower motor 140. For example, the blower motor 140 may control the impeller 120 such that a volume of air may be dispensed from a respirator air outlet at a respirator output flowrate. In various embodiments, the output flowrate of a respirator may vary based at least in part on one or more blower motor operating parameters, such as, for example, motor speed (e.g., motor revolutions per minute (RPM)), motor voltage, motor current, and/or the like. For example, in a respirator system 10 experiencing zero back pressure, the relationship between respirator output flowrate and motor speed is approximately linear, such that the respirator output flowrate may increase approximately linearly with an increase in motor speed. Similarly, in a zero-back-pressure respirator system, the respirator output flowrate may likewise increase approximately linearly with an increase in motor voltage. Further, with an increase in motor current the respirator output flowrate increases approximately exponentially at lower flowrates and evolves to an approximately linear relationship at higher flowrates. Accordingly, because the respirator output flowrate may be directly proportional to motor speed, the respirator output flowrate of a respirator 10 may be indirectly monitored based at least in part on the motor speed of the blower motor 140. Further, in various embodiments, the motor speed of a blower motor 140 may have a linear and directly proportional relationship to the motor voltage of the blower motor 140. In such a circumstance, as described herein, motor voltage may be controlled using pulse-width modulation (PWM) to either increase or decrease the motor speed in order to selectively increase or decrease the corresponding respirator output airflow of the respirator 10.

In various embodiments, the pulse with modulation configuration of a blower motor 140 may be controlled so as to selectively adjust the motor voltage in order to maintain an at least substantially consistent respirator output airflow. For example, the pulse width modulation configuration of an exemplary blower motor may be defined at least in part by a duty cycle. As described herein, the duty cycle of a PWM voltage signal may be defined as the proportion of the PWM voltage signal that is held in an "on state" relative to the total voltage signal (e.g. the percentage of the total voltage signal that is applied to a blower motor). In various embodiments, a full duty cycle of a PWM voltage signal may comprise a range of pulse width modulation configurations between a fully "off" and a fully "on" PWM voltage signal, which may be defined be a plurality of steps. For example, each of the plurality of steps of a PWM voltage signal may be associated with a respective duty cycle count that corresponds to a particular duty cycle of the PWM voltage signal. In such a circumstance, each duty cycle count of the pulse width modulation configuration may correspond to an incremental voltage step that corresponds to a fraction of the maximum motor voltage of the blower motor. As described herein, the duty cycle count of the PWM voltage signal (e.g., of the pulse width modulation configuration of a blower motor) may be described as a motor PWM of a blower motor, wherein a change in the motor PWM is defined by a change in the duty cycle count of the blower motor. As such, the motor voltage of a blower motor may be selectively varied by selectively increasing/decreasing motor PWM (e.g., the duty cycle count of the PWM voltage signal) of the blower motor.

In various embodiments, wherein the respirator output airflow of a respirator 10 is maintained as constant, the relationship between the motor PWM and the motor speed over a full blower motor operational range, (e.g., at various system back pressures) is approximately linear. As described herein, when the blower assembly 100 of a respirator 10 is operating such that the amount of air being pushed out of the blower assembly outlet 113 is greater than the amount of air being pulled into the blower assembly inlet 111, a back pressure is created. A respirator 10 may be configured so as to define an operable range in which the blower assembly 100 can continue to operate, wherein the maximum blower operational capacity (e.g., the maximum blower production output) is defined as the maximum back pressure that the blower can drive. The full blower motor operational range of the blower assembly 100 may extend between a minimum blower production output (e.g., 0 mm $H_2O$) and the aforementioned maximum blower production output. In such an exemplary circumstance, as the system back pressure driven by a blower assembly 100 fluctuates between a minimum blower production output (e.g., 0 mm $H_2O$) and a maximum blower production output, the relationship between the motor PMW and the motor speed required to maintain an at least substantially consistent respirator output flowrate is at least approximately linear such that the motor PMW is directly proportional to the motor speed under a constant respirator output flowrate condition. Similarly, under a constant output flowrate condition, the motor current of a blower motor 140 may likewise be directly proportional to the motor PWM so as to define an approximately linear relationship between the two blower motor operating parameters over the full blower motor operational range. For example, in various embodiments, the exemplary apparatus and method described herein may provide a substantially consistent respirator output airflow that is greater than 170 LPM with a nominal output airflow of 190 LPM when used with a variety of loose fit hoods and helmets.

Figure 2:
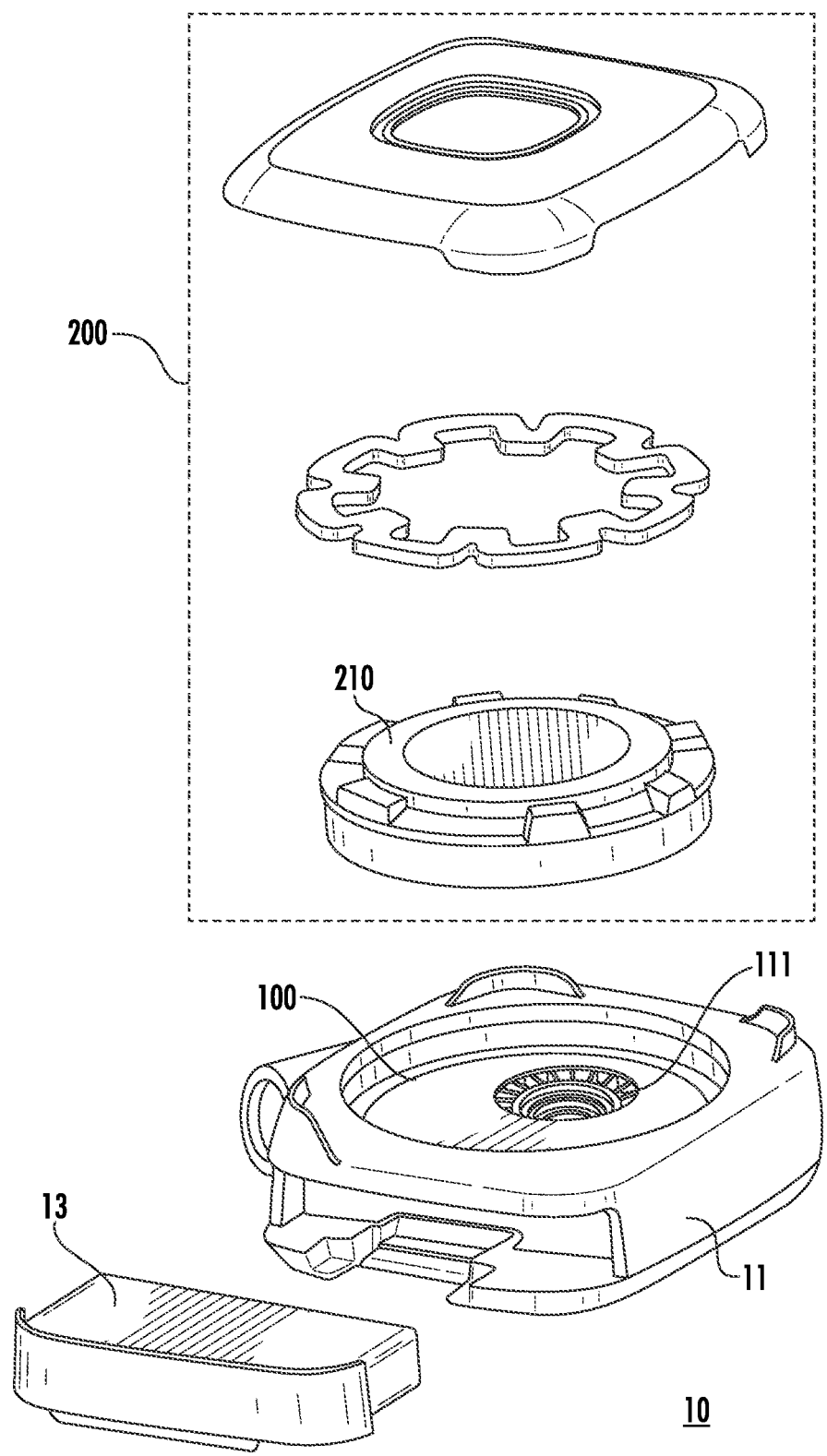
FIG. 2 illustrates an exploded perspective view of various components of an exemplary respirator apparatus in accordance with various embodiments.

FIG. 2 illustrates an exploded perspective view of various components of an exemplary respirator apparatus in accordance with various embodiments. In particular, FIG. 2 illustrates an exploded bottom perspective view of an exemplary filter assembly 200 arranged relative to a respirator housing 11 in accordance with various embodiments. In various embodiments, an exemplary respirator 10 described herein may further comprise a filter assembly 200 configured to extract various contaminants from within a volume of air received from an ambient environment by the respirator 10. The filter assembly 200 may be configured to at least partially purify the volume of air prior to the volume of air being dispensed into a controlled environment. In various embodiments, the filter assembly 200 may define at least a portion of the respirator air flow path such that a volume of air traveling from the respirator air inlet and along the respirator air flow path may pass through the filter assembly 200. For example, the filter assembly 200 may comprise a filter element 210 configured to capture various contaminates such as, for example, particulate matter, airborne bacteria, and/or the like, from the volume of air traveling along the respirator air flow path. As a non-limiting example, in various embodiments, the filter element 210 may comprise one or both of a physical filter media and a chemical filter media. In various embodiments, the filter media of the filter element 210 may be configured based at least in part on a particular contaminant and/or type of contaminant that is sought to be extracted from the volume of ambient air traveling therethrough. In various embodiments, the filter assembly 200 may be positioned upstream from the respirator air outlet such that the contaminants present within the volume of ambient air received by the respirator 10 are extracted prior to the volume of air being dispensed into the controlled environment, thereby minimizing the amount of contaminant within the purified air of the controlled environment. Such an exemplary configuration may minimize the amount of contaminant within the purified air of the controlled environment.

In various embodiments, the respirator output flowrate of a respirator 10 may be affected by one or more respirator operational conditions, such as, for example, the system back pressure within the respirator 10. For example, in an exemplary circumstance wherein the motor voltage of a blower motor is maintained as constant, an increased system back pressure experienced at the blower assembly outlet may result in a decreased respirator output flowrate. Similarly, the respirator may be configured such that as a back pressure at the blower outlet increases, the load placed on the blower motor decreases, resulting in an increased motor speed under a constant motor voltage condition. Further, as a back pressure at the blower outlet increases, the motor current may remain at least substantially the same (e.g., negligible motor current variances). In various embodiments wherein the respirator 10 comprises, for example, a filter assembly 200 that is fluidly connected along the air flow path to an impeller of a blower assembly, the filter assembly 200 may correspond to a pressure drop within the respirator 10 along the respirator air flow path. For example, in an exemplary circumstance wherein a filter assembly 200 is positioned upstream from a blower assembly air inlet 111, as illustrated in FIG. 2, the filter assembly pressure drop may decrease the pressure at blower assembly air inlet 111, which may affect one or more blower motor operating parameters and/or respirator output flowrate, as described above. As the filter assembly (e.g., the filter element 210) accumulates an increasing amount of contaminate and becomes increasingly clogged over time (e.g., between a new, unclogged filter and a fully clogged filter), the pressure drop over the filter assembly 200 also increases, which may affect one or more blower motor operating parameters. For example, an increase in the extent of filter blockage may lead to a decreased respirator output flowrate and an increased motor speed and decreased motor current under a constant motor voltage condition. As described herein, a system pressure resulting in an increased motor speed without a corresponding increased respirator output flowrate causes the relationship between the motor speed and the respirator output flowrate to deviate from its aforementioned approximately linear relationship. In such an exemplary circumstance, the motor speed of a blower motor may not be representative of the respirator output flowrate at a given instance. As described herein, an exemplary respirator 10 may be configured to programmatically adjust one or more blower motor operating parameters to compensate for variations in one or more respirator operational conditions, such as, for example, filter blockage of the filter assembly 200, in order to maintain an at least substantially consistent respirator output flowrate.

In various embodiments, the respirator housing 11 may be further configured to house a removeable power source 13, such as, for example, a battery, configured to supply power to one or more electrical components of the respirator 10. In various embodiments, the removeable power source 13 may comprise a rechargeable battery cartridge and/or one or more replaceable batteries. Further, as described herein, an exemplary respirator 10 may comprise various sensors configured to facilitate the generation of blower motor data and/or ambient environment characterization data. For example, in various embodiments, an exemplary respirator 10 may comprise one or more blower motor speed sensors configured to measure the motor speed of the blower motor 140 at one or more instances so as to facilitate the generation of measured motor speed data. As a non-limiting example, the one or more blower motor speed sensors may comprise one or more Hall sensors configured to measure the motor speed of the blower motor 140 based at least in part on the position of the rotor assembly of the blower motor 140. Further, in various embodiments, an exemplary respirator 10 may comprise an ambient temperature sensor, such as, for example, a thermometer, configured to measure the ambient temperature of an ambient environment in which the respirator 10 is located at one or more instances so as to facilitate the generation of ambient environment characterization data. Further, in various embodiments, an exemplary respirator 10 may comprise an ambient pressure sensor configured to measure the ambient pressure within an ambient environment in which the respirator 10 is located at one or more instances so as to facilitate the generation of ambient environment characterization data. For example, an ambient pressure sensor may be used to facilitate the altitude compensation functionality of the exemplary respirator 10, as described herein. Alternatively, or additionally, the exemplary respirator 10 may comprise an ambient position sensor, such as, for example, a global positioning system, configured to measure the altitude at which the respirator 10 is located at one or more instances in order to facilitate the altitude compensation functionality of the exemplary respirator 10. In various embodiments, each of the various sensors of the respirator 10 housed within the respirator housing 11 may by electronically connected to PCBA 150 (e.g., a controller), as described herein, to facilitate the transfer of one or more signals therebetween in order to execute various operations described herein.

Figure 3:
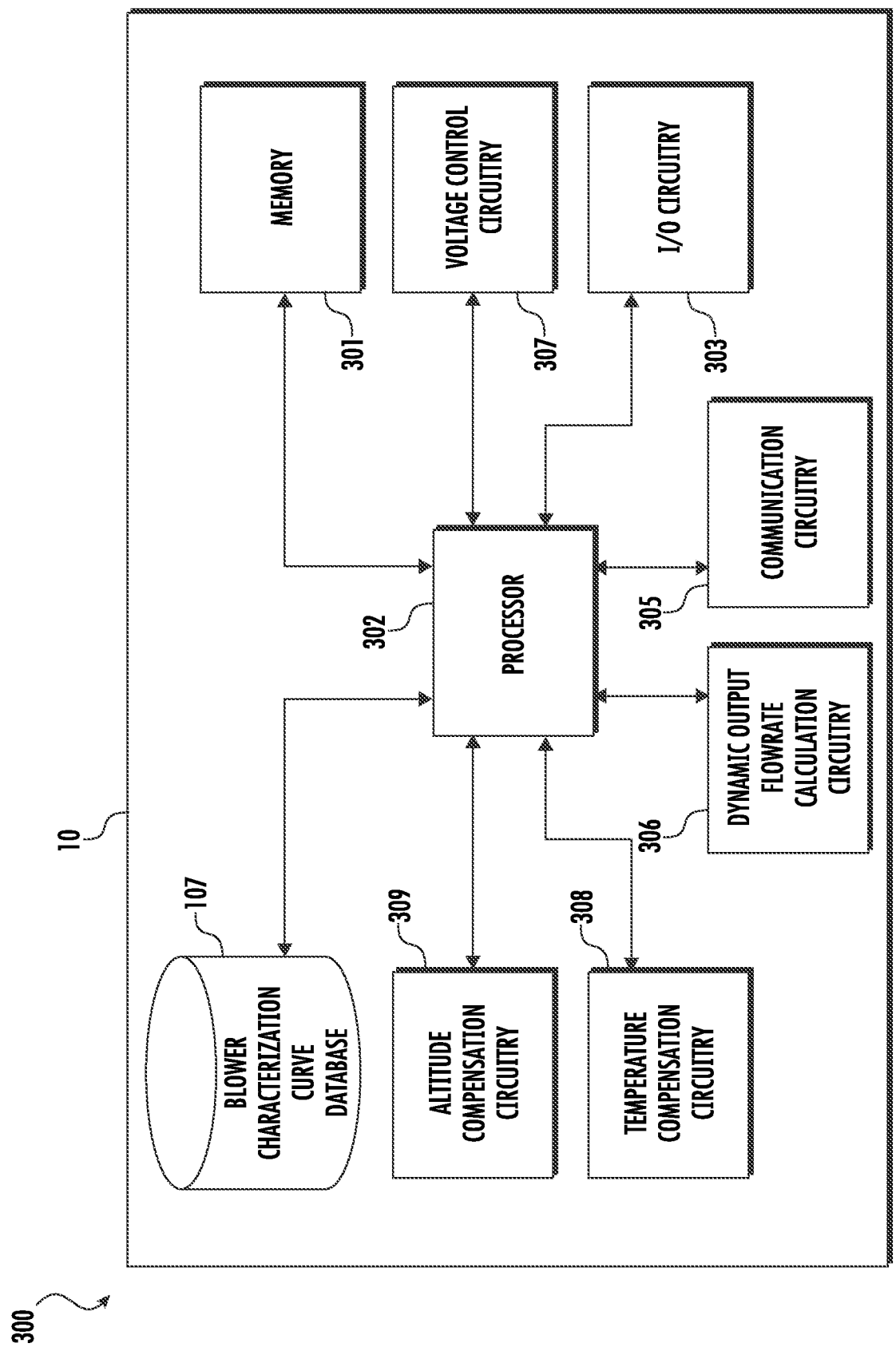
FIG. 3 schematically illustrates an exemplary apparatus for implementing various embodiments of the present disclosure.

As shown in FIG. 3, the respirator 10 may comprise a controller 300 configured to control the various operations associated with the consistent output flowrate delivery function of an exemplary respirator 10 described herein. As illustrated in FIG. 3, the controller 300 may comprise a memory 301, a processor 302, input-output circuitry 303, communication circuitry 305, a blower characterization curve database 107, a dynamic output flowrate calculation circuitry 306, voltage control circuitry 307, temperature compensation circuitry 308, and altitude compensation circuitry 309. The controller 300 may be configured to execute the operations described herein. Although the components are described with respect to functional limitations, it should be understood that the particular implementations necessarily include the use of particular hardware. It should also be understood that certain of the components described herein may include similar or common hardware. For example, two sets of circuitry may both leverage use of the same processor, network interface, storage medium, or the like to perform their associated functions, such that duplicate hardware is not required for each set of circuitry. The use of the term "circuitry" as used herein with respect to components of the controller 300 should therefore be understood to include particular hardware configured to perform the functions associated with the particular circuitry as described herein.

The term "circuitry" should be understood broadly to include hardware and, in some embodiments, software for configuring the hardware. For example, in some embodiments, "circuitry" may include processing circuitry, storage media, network interfaces, input/output devices, and the like. In some embodiments, other elements of the controller 300 may provide or supplement the functionality of particular circuitry. For example, the processor 302 may provide processing functionality, the memory 301 may provide storage functionality, the communication circuitry 305 may provide network interface functionality, and the like.

In some embodiments, the processor 302 (and/or co-processor or any other processing circuitry assisting or otherwise associated with the processor) may be in communication with the memory 301 via a bus for passing information among components of the apparatus. The memory 301 may be non-transitory and may include, for example, one or more volatile and/or non-volatile memories. For example, the memory 301 may be an electronic storage device (e.g., a computer readable storage medium). In various embodiments, the memory 301 may be configured to store information, data, content, applications, instructions, or the like, for enabling the apparatus to carry out various functions in accordance with example embodiments of the present disclosure. It will be understood that the memory 301 may be configured to store partially or wholly any electronic information, data, data structures, embodiments, examples, figures, processes, operations, techniques, algorithms, instructions, systems, apparatuses, methods, look-up tables, or computer program products described herein, or any combination thereof. As a non-limiting example, the memory 301 may be configured to store blower motor data, calibrated motor data, ambient environment characterization data, one or more derived blower characterization equations, one or more material property look-up tables, and/or the like.

The processor 302 may be embodied in a number of different ways and may, for example, include one or more processing devices configured to perform independently. Additionally or alternatively, the processor may include one or more processors configured in tandem via a bus to enable independent execution of instructions, pipelining, and/or multithreading. The use of the term "processing circuitry" may be understood to include a single core processor, a multi-core processor, multiple processors internal to the apparatus, and/or remote or "cloud" processors.

In an example embodiment, the processor 302 may be configured to execute instructions stored in the memory 301 or otherwise accessible to the processor. Alternatively, or additionally, the processor may be configured to execute hard-coded functionality. As such, whether configured by hardware or software methods, or by a combination thereof, the processor may represent an entity (e.g., physically embodied in circuitry) capable of performing operations according to an embodiment of the present disclosure while configured accordingly. Alternatively, as another example, when the processor is embodied as an executor of software instructions, the instructions may specifically configure the processor to perform the algorithms and/or operations described herein when the instructions are executed.

In some embodiments, the controller 300 may include input-output circuitry 303 that may, in turn, be in communication with the processor 302 to provide output to the user and, in some embodiments, to receive input such as a command provided by the user. The input-output circuitry 303 may comprise a user interface, such as a graphical user interface (GUI), and may include a display that may include a web user interface, a GUI application, a mobile application, a client device, or any other suitable hardware or software. In some embodiments, the input-output circuitry 303 may also include a display device, a display screen, user input elements, such as a touch screen, touch areas, soft keys, a keyboard, a mouse, a microphone, a speaker (e.g., a buzzer), a light emitting device (e.g., a red light emitting diode (LED), a green LED, a blue LED, a white LED, an infrared (IR) LED, an ultraviolet (UV) LED, or a combination thereof), or other input-output mechanisms. The processor 302, input-output circuitry 303 (which may utilize the processing circuitry), or both may be configured to control one or more functions of one or more user interface elements through computer-executable program code instructions (e.g., software, firmware) stored in a non-transitory computer-readable storage medium (e.g., memory 301). Input-output circuitry 303 is optional and, in some embodiments, the controller 300 may not include input-output circuitry. For example, where the controller 300 does not interact directly with the user, the controller 300 may generate user interface data for display by one or more other devices with which one or more users directly interact and transmit the generated user interface data to one or more of those devices. For example, the controller 300, using user interface circuitry may generate user interface data for display by one or more display devices and transmit the generated user interface data to those display devices.

The communication circuitry 305 may be a device or circuitry embodied in either hardware or a combination of hardware and software that is configured to receive and/or transmit data from/to a network and/or any other device, circuitry, or module in communication with the controller 300. For example, the communication circuitry 305 may be configured to communicate with one or more computing devices via wired (e.g., USB) or wireless (e.g., Bluetooth, Wi-Fi, cellular, and/or the like) communication protocols.

In various embodiments, the processor 302 may be configured to communicate with the dynamic output flowrate calculation circuitry 306. The dynamic output flowrate calculation circuitry 306 may be a device or circuitry embodied in either hardware or a combination of hardware and software that is configured to receive, process, generate, and/or transmit data, such as, for example, blower motor data and/or calibrated motor data in order to determine whether the blower motor of an exemplary respirator is operating so as to produce a respirator output flowrate that is at least substantially consistent with a desired respirator output flowrate. In various embodiments, the dynamic output flowrate calculation circuitry 306 may be configured to receive various blower motor data associated with a first instance. In various embodiments, the dynamic output flowrate calculation circuitry 306 may be configured to retrieve various calibrated motor data identifying a plurality of motor output calibration points and selectively retrieve a derived blower characterization equation based on a determined blower motor operational range of the blower motor at the first instance. The dynamic output flowrate calculation circuitry 306 may be configured to programmatically determine a first optimized motor speed by utilizing the retrieved blower characterization equation to analyze the blower motor data associated with the first instance and determine a motor speed at which an exemplary blower motor exhibiting a first motor PWM should be operating in order to produce a desired respirator output flowrate. The dynamic output flowrate calculation circuitry 306 may receive a motor speed temperature compensation factor and a motor speed pressure compensation factor from the temperature compensation circuitry 308 and the altitude compensation circuitry 309, respectively. Further, the dynamic output flowrate calculation circuitry 306 may calculate an adjusted measured motor speed corresponding to the first instance based at least in part on the calculated first optimized motor speed and one or both of the motor speed temperature compensation factor and the motor speed pressure compensation factor, so as to compensate for the effect of the altitude (e.g., ambient pressure) and/or the ambient temperature on the blower assembly of the respirator 10. In various embodiments, the dynamic output flowrate calculation circuitry 306 may be configured to execute one or more of the operations described herein at two or more instances, so as to facilitate the calculation of an adjusted measured motor speed corresponding to various instances over time. Further, the dynamic output flowrate calculation circuitry 306 may be configured to transmit data such as a programmatically determined optimized motor speed and an adjusted measured motor speed, each associated with the same instance, to the voltage control circuitry 307. In various embodiments, the dynamic output flowrate calculation circuitry 306 may send and/or receive data from the blower characterization curve database 107. Further, in various embodiments, although described above with respect to an exemplary circumstance wherein motor speed is used as an indicator of respirator output flowrate, the dynamic output flowrate calculation circuitry 306 may be configured to execute one or more similar operations wherein the motor current of the blower motor is used as an indicator of respirator output flowrate, as described herein.

In various embodiments, the processor 302 may be configured to communicate with the voltage control circuitry 307. The voltage control circuitry 307 may be a device or circuitry embodied in either hardware or a combination of hardware and software that is configured to programmatically adjust a motor voltage of a blower motor in order to configure the blower motor to produce a respirator output flowrate that is at least substantially consistent with the desired respirator output flowrate. In various embodiments, the voltage control circuitry 307 may be configured to receive programmatically determined blower motor data associated with a first instance from the dynamic output flowrate calculation circuitry 306, such as, for example, an optimized motor speed and an adjusted measured motor speed. The voltage control circuitry 307 may be configured to compare an optimized motor speed and an adjusted measured motor speed associated with an instance. In various embodiments, the voltage control circuitry 307 may be configured to retrieve various data identifying an exemplary acceptable measured motor speed tolerance range and/or an acceptable respirator output flowrate tolerance range. The voltage control circuitry 307 may be configured to determine whether the adjusted measured motor speed associated with an instance is within exemplary acceptable measured motor speed tolerance range, based at least in part on the optimized motor speed at the instance. Further, in various embodiments, the voltage control circuitry 307 may be configured to, upon determining that the adjusted measured motor speed associated with an instance is not within the exemplary acceptable measured motor speed tolerance range, programmatically adjust the motor PWM of the blower motor in order to order to adjust the motor speed such that the respirator output flowrate produced by the blower motor may remain at least substantially consistent with a desired respirator output flowrate. In various embodiments, the voltage control circuitry 307 may be configured to execute one or more of the operations described herein at two or more instances, so as to maintain an at least substantially consistent respirator output flowrate at various instances over time, as described herein. In various embodiments, the voltage control circuitry 307 may send and/or receive data from the blower characterization curve database 107.

The temperature compensation circuitry 308 may be a device or circuitry embodied in either hardware or a combination of hardware and software that is configured determine a motor speed temperature compensation factor to be applied to various measured blower motor data in order to compensate for the effect of the ambient temperature on the blower assembly of the respirator 10, as described herein. In various embodiments, the temperature compensation circuitry 308 may be configured to receive ambient environment characterization data, such as, for example, measured ambient temperature data, associated with an instance. The temperature compensation circuitry 308 may be configured to calculate a motor speed temperature compensation factor, as described herein, in order to compensate for the effect of the measured ambient temperature on the blower assembly of the respirator 10. In various embodiments, the temperature compensation circuitry 308 may be configured to retrieve blower motor data in order to calculate the motor speed temperature compensation factor at a first instance. Further, in various embodiments, the temperature compensation circuitry 308 may send and/or receive data from the memory 301 such as, for example, one or more material property look-up tables, in order to determine a motor speed temperature compensation factor. In various embodiments, the temperature compensation circuitry 308 may be configured to execute one or more of the operations described herein at two or more instances, so as to facilitate the determination of various motor speed temperature compensation factors corresponding, respectively, to various instances over time.

The altitude compensation circuitry 309 may be a device or circuitry embodied in either hardware or a combination of hardware and software that is configured determine a motor speed pressure compensation factor to be applied to various measured blower motor data in order to compensate for the effect of the ambient pressure (e.g., an altitude) on the blower assembly of the respirator 10, as described herein. In various embodiments, the altitude compensation circuitry 309 may be configured to receive ambient environment characterization data, such as, for example, measured ambient pressure data and/or measured ambient altitude data, associated with an instance. In various embodiments, the altitude compensation circuitry 309 may be configured to determine an ambient pressure at an instance based at least in part on a measured ambient altitude at that instance. For example, the altitude compensation circuitry 309 may send and/or receive data from the memory 301 such as, for example, one or more equations defining a relationship between an ambient altitude and an ambient pressure. The altitude compensation circuitry 309 may be configured to calculate a motor speed pressure compensation factor, as described herein, in order to compensate for the effect of an ambient pressure on the blower assembly of the respirator 10. For example, in various embodiments, the altitude compensation circuitry 309 may be configured to retrieve various blower motor data in order to derive a relationship between an ambient pressure and a corresponding motor speed pressure compensation factor, as described herein. In various embodiments, the altitude compensation circuitry 309 may be configured to execute one or more of the operations described herein at two or more instances, so as to facilitate the determination of various motor speed pressure compensation factors corresponding, respectively, to various instances over time.

In various embodiments, the respirator 10 may be configured with, or in communication with, a blower characterization curve database 107. The blower characterization curve database 107 may be stored, at least partially on the memory 301 of the system. In some embodiments, the blower characterization curve database 107 may be remote from, but in connection with, the respirator 10. The blower characterization curve database 107 may be configured to store information, such as, for example, calibrated motor data. The calibrated motor data stored in the blower characterization curve database 107 may comprise data defining each of the plurality of motor output calibration points, such as, for example, an exemplary table comprising various calibrated motor data associated with each motor output calibration point. Further, the calibrated motor data stored in the blower characterization curve database 107 may comprise the one or more blower characterization equations corresponding to the one or more blower motor operational ranges defined by the plurality of motor output calibration points. In various embodiments, the blower characterization curve database 107 may be further configured to store various blower motor data associated with one or more instances, as described herein.

Figure 4:
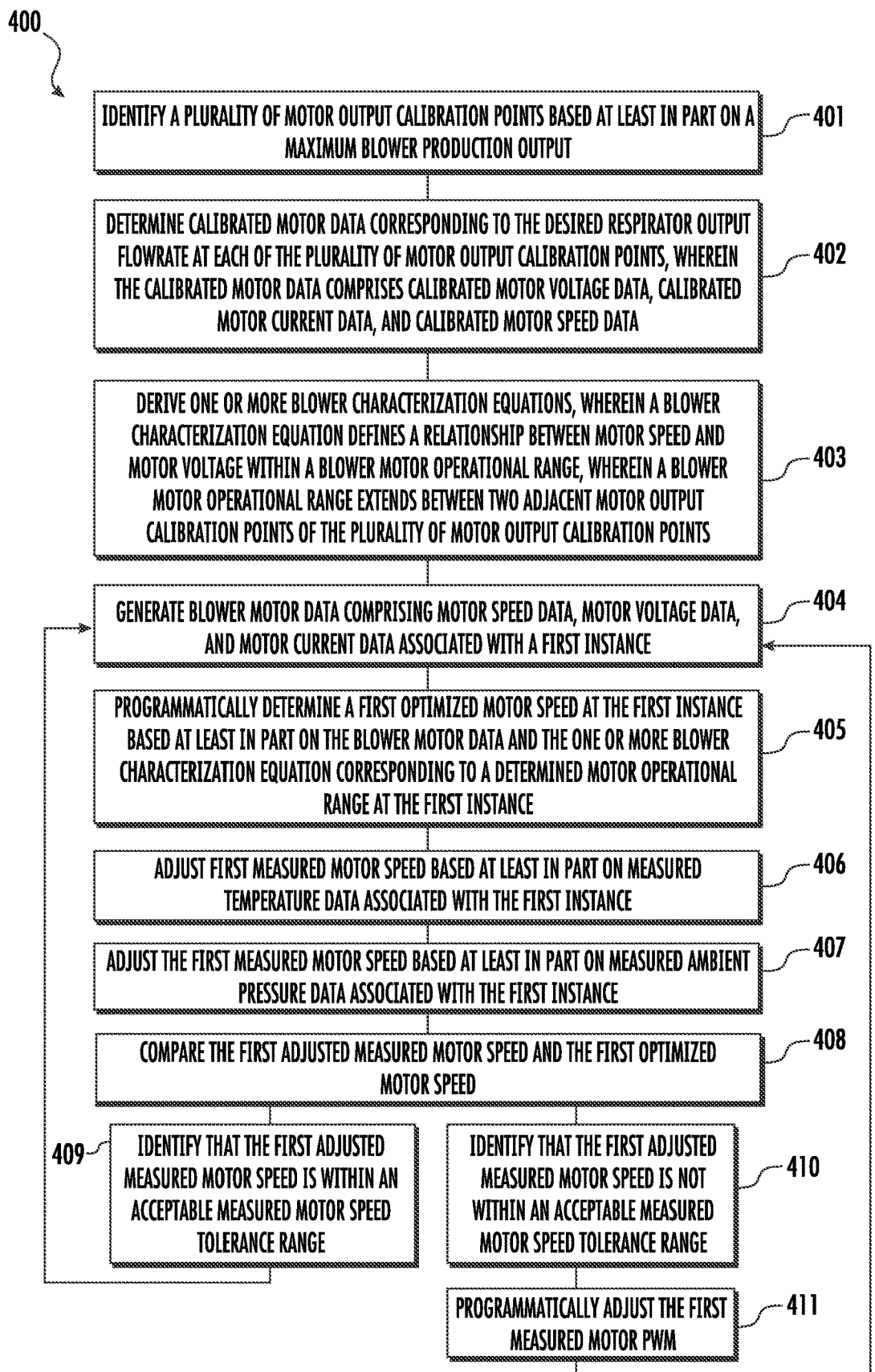
FIG. 4 is a flowchart illustrating example steps for generating an at least substantially consistent output airflow from a respirator in accordance with various embodiments.

FIG. 4 is a flowchart illustrating example steps for generating an at least substantially consistent output airflow from a respirator in accordance with various embodiments. As shown in FIG. 4, an at least substantially consistent respirator output flowrate may be produced by dynamically analyzing and selectively adjusting one or more blower motor operating parameters based at least in part on one or more derived blower characterization equations corresponding to a respective blower motor operational range. The exemplary method 400 begins at Block 401, with identifying a plurality of motor output calibration points based at least in part on a maximum blower production output. The maximum blower production output (e.g., the maximum operational capacity of a blower motor) may be characterized by a maximum amount of pressure that can be driven by a blower motor. For example, a blower motor driving a back pressure that is less than the maximum amount of pressure that the blower motor can drive may be operating at less than the maximum operational capacity of the blower, which may be defined as a partial blower production output. In such a circumstance, a partial blower production output may be represented as a percentage of the maximum blower production output of the blower motor. In order to more accurately characterize the dynamic behavior of the respirator blower assembly (e.g., the blower motor) over the full blower motor operational range, a plurality of motor output calibration points may be identified so as to define one or more blower motor operational ranges, as described herein. For example, each of the plurality of motor output calibration points may correspond to a distinct blower production output (e.g., at a minimum blower production output, at a maximum blower production output, and/or at a partial blower production output therebetween) for an exemplary respirator configured to produce a desired respirator output flowrate. As described herein, each calibration point may function as a defined blower motor operating state at which one or more of the blower motor operating parameters are to be defined so as to facilitate an accurate approximation of one or more other blower motor operating parameters.

In various embodiments, the maximum blower production output of the blower motor of a respirator may be known, calculated, and/or determined empirically. As a non-limiting example, a blower motor of an exemplary respirator may have a maximum operational capacity of 68 mm $H_2O$. In such an exemplary circumstance, the full blower motor operational range extends from the minimum blower production output of 0 mm $H_2O$ to the maximum blower production output of 68 mm $H_2O$. For example, the minimum blower production output and the minimum blower production output may each be identified as a calibration point. Further, in various embodiments, the plurality of motor output calibration points may include additional motor output calibration points at intermittent partial blower production outputs within the full blower motor operational range. In various embodiments, the number of motor output calibration points used may be selected based on various considerations such as, for example, the additional production time and costs associated with manufacturing a respirator configured to utilize a greater number of motor output calibration points, and the extent to which the accuracy of the blower characterization is increased by the more granular blower motor characterization facilitated by additional motor output calibration points. For example, at least substantially between one and twenty motor output calibration points may be identified. More preferably, at least substantially between one and ten motor output calibration points may be identified. Most preferably, at least substantially between two and four motor output calibration points may be identified. In various embodiments, each calibration point may be identified such that the plurality of calibrations points are at least substantially evenly distributed throughout the full blower motor operational range. For example, in an exemplary circumstance wherein the maximum blower production output of a blower motor is 68 mm $H_2O$, the plurality of motor output calibration points may include three motor output calibration points identified, respectively, as a first calibration point at 0 mm $H_2O$, a second calibration point at 34 mm $H_2O$, and a third calibration point at 68 mm $H_2O$. As a further non-limiting example, in the exemplary circumstance wherein the maximum blower production output of a blower motor is 68 mm $H_2O$, the plurality of motor output calibration points may include four motor output calibration points identified, respectively, as a first calibration point at 0 mm $H_2O$, a second calibration point at 22 mm $H_2O$, a third calibration point at 46 mm $H_2O$, and a fourth calibration point at 68 mm $H_2O$.

At Block 402, calibrated motor data corresponding to a desired respirator output flowrate may be measured at each of the plurality of motor output calibration points. In various embodiments, the calibrated motor data may comprise calibrated motor voltage data, calibrated motor current data, and calibrated motor speed data for an exemplary blower motor corresponding to a motor output calibration point, wherein the blower motor is configured to produce the desired respirator output flowrate. In various embodiments, calibrated motor data may be either calculated or determined empirically.

Figure 5:
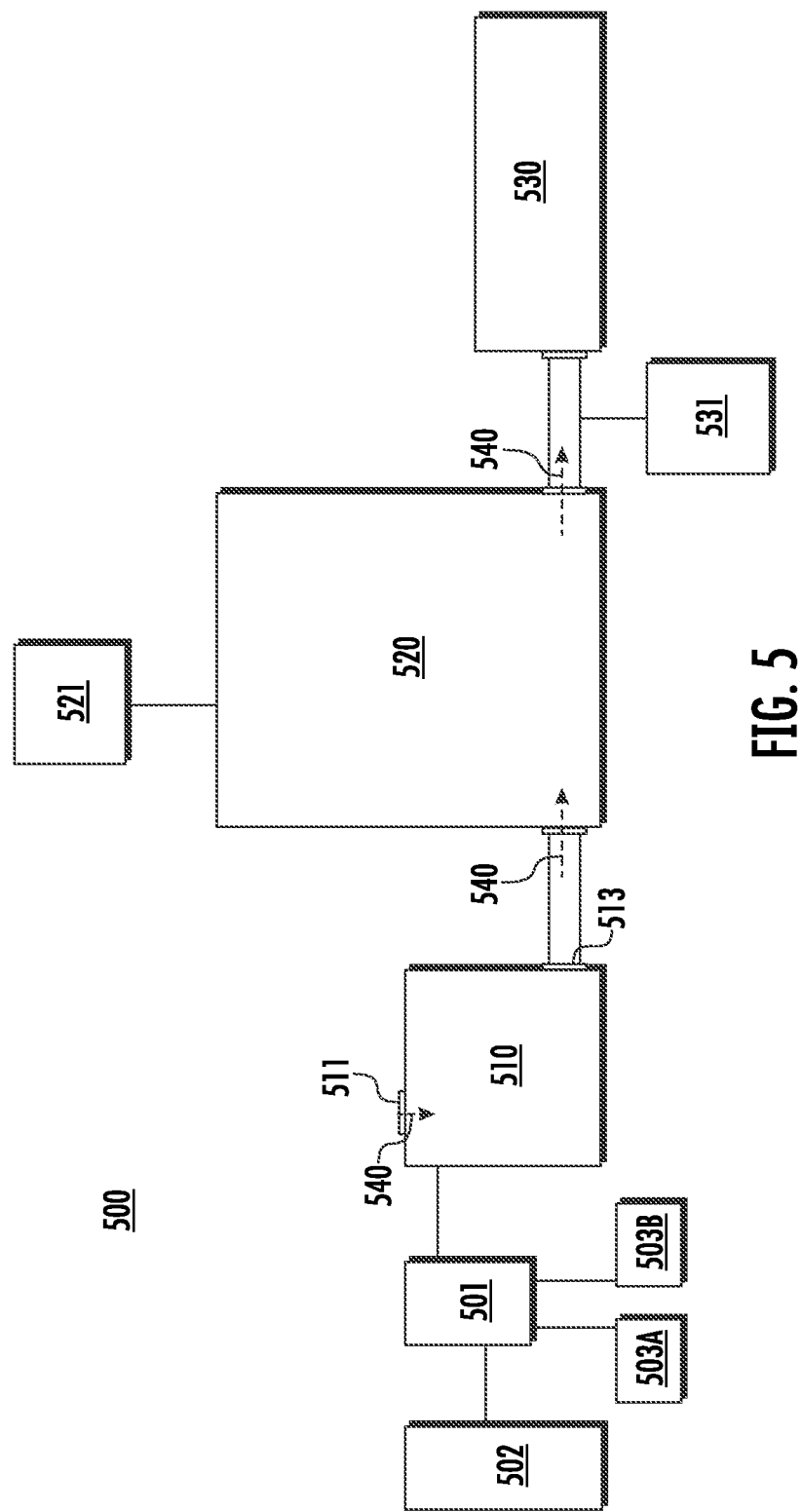
FIG. 5 shows an exemplary test configuration in accordance with various embodiments.

FIG. 5 schematically illustrates an exemplary test configuration 500 that may be utilized to determine calibrated motor data in accordance with various embodiments. For example, exemplary test configuration 500 may comprise an exemplary blower assembly 510 that is electronically connected to a blower motor 501 that is configured to control the operation of the blower motor 510, as described herein. For example, the blower motor 501 may be configured one or more electrical signals may be received from and/or transmitted to a PCBA 502 such that one or more blower motor operating parameters of the blower motor 501 may be selectively controlled and/or measured. The PCBA 502 may be configured to dynamically measure the motor voltage (e.g., the motor PWM) of the blower motor 501 at a given instance. Further, one or more blower motor operating parameter measurement devices 503A-503B may be connected to the blower motor 501 and configured to dynamically measure one or more blower motor operating parameters. For example, at least a portion of the one or more blower motor operating parameter measurement devices 503A-503B may be configured to measure the motor voltage, motor speed, and/or motor current of the blower motor 510 at a given instance. The blower motor operating parameter measurement devices 503A-503B may comprise a voltmeter, a Hall sensor, an ammeter, and/or the like.

The blower assembly 510 may comprise an impeller configured according to various embodiments described herein. The exemplary blower assembly 510 may comprise a blower air inlet 511 through which the impeller may pull an ambient volume of air into the blower assembly 510, and a blower air outlet 513 from which the impeller may pushed the ambient volume of air. As illustrated, the exemplary test configuration 500 may comprise a flow chamber 520 positioned downstream from blower air outlet 513 of the blower assembly 510 such that the volume of air dispensed may travel to the flow chamber 520. In operation, the flow chamber 520 may be configured to represent a portion of an exemplary respirator system such as, for example, a respirator air flow path positioned downstream from an exemplary blower assembly. The exemplary test configuration 500 may comprise a pressure sensor 521 such as, for example, a manometer configured to measure the pressure within the flow chamber 520 at a given instance. For example, the pressure within the flow chamber 520 at a given instance may correspond to a back pressure within an exemplary respirator system. Additionally, the exemplary test configuration 500 may comprise an air vacuum positioned downstream from the flow chamber 530 and configured to pull air from within the flow chamber 520 into the air vacuum 530. The air vacuum 530 may be configured such that the operation settings of the air vacuum 530 (e.g., the input power) may be selectively adjusted in order to selectively control the pressure within the flow chamber 520. As illustrated, the blower chamber 510, the flow chamber 520, and the air vacuum 530 may be fluidly connected such that the exemplary test configuration 500 defines an air flow path 540 extending from the blower air inlet 511, through the blower air outlet 513 to the flow chamber 520, and further to the air vacuum 530. Further, the exemplary test configuration 500 may comprise a flowmeter 531 arranged along the fluid flow path 540 and configured to measure the output rate of air exiting the flow chamber 520 at a given instance. For example, the exemplary test configuration 500 may be configured such that the output of the flowmeter 531 may correspond to a respirator output flowrate of an exemplary respirator comprising the blower assembly 510, as described herein.

In various embodiments, in a pre-production circumstance, for example, a back pressure load corresponding to a first motor output calibration point may be selectively applied to a blower assembly 510 in operation, for example, by selectively adjusting the configuration (e.g., the input power) of the air vacuum 530. The motor PMW (e.g., motor voltage) of the blower motor 501 may be selectively adjusted in order to produce a measured respirator output flowrate that is at least substantially equal to a predetermined desired respirator output flowrate. At a first instance when the measured respirator output flowrate (e.g., the output reading of the flowmeter 531) is at least substantially equal to the desired respirator output flowrate, the motor PWM, the motor speed, and the motor current are recorded using at least a portion of the blower motor operating parameter measurement devices 503A-503B and/or the PCBA 502. The recorded motor PWM, motor speed, and motor current define, at least in part, the calibrated motor data, calibrated motor speed data, and calibrated motor current data, respectively, and collectively define the calibrated motor data corresponding to the first motor output calibration point. In various embodiments, the back pressure load applied to system, which must be overcome by blower motor 501 in order for the blower assembly 510 to operate, may be iteratively adjusted so as to reflect each of the plurality of motor output calibration points. Calibrated motor data (e.g., calibrated motor voltage data, calibrated motor speed data, and calibrated motor current data) corresponding to the desired respirator output flowrate may be determined at each of the motor output calibration points.

As a non-limiting example, in an exemplary circumstance wherein the plurality of motor output calibration points includes a first calibration point at 0 mm $H_2O$, a second calibration point at 22 mm $H_2O$, a third calibration point at 46 mm $H_2O$, and a fourth calibration point at 68 mm $H_2O$, calibrated motor voltage data, calibrated motor speed data, and calibrated motor current data is determined at each of the four motor output calibration points. By way of non-limiting illustrative example, Table 1, below, includes exemplary calibrated motor data that may be determined in such an exemplary circumstance:

| Motor Output Calibration Point | Back Pressure (mm H2O) | Respirator Output Airflow (LPM) | Motor PWM | Motor Speed (RPM) | Motor Current (A) |
| --- | --- | --- | --- | --- | --- |
| 1 | 0 | 190 | 354 | 4667 | 0.3153 |
| 2 | 22 | 190 | 404 | 6534 | 0.5208 |
| 3 | 46 | 190 | 456 | 8110 | 0.8089 |
| 4 | 68 | 190 | 496 | 9384 | 1.1655 |

Figure 6A:
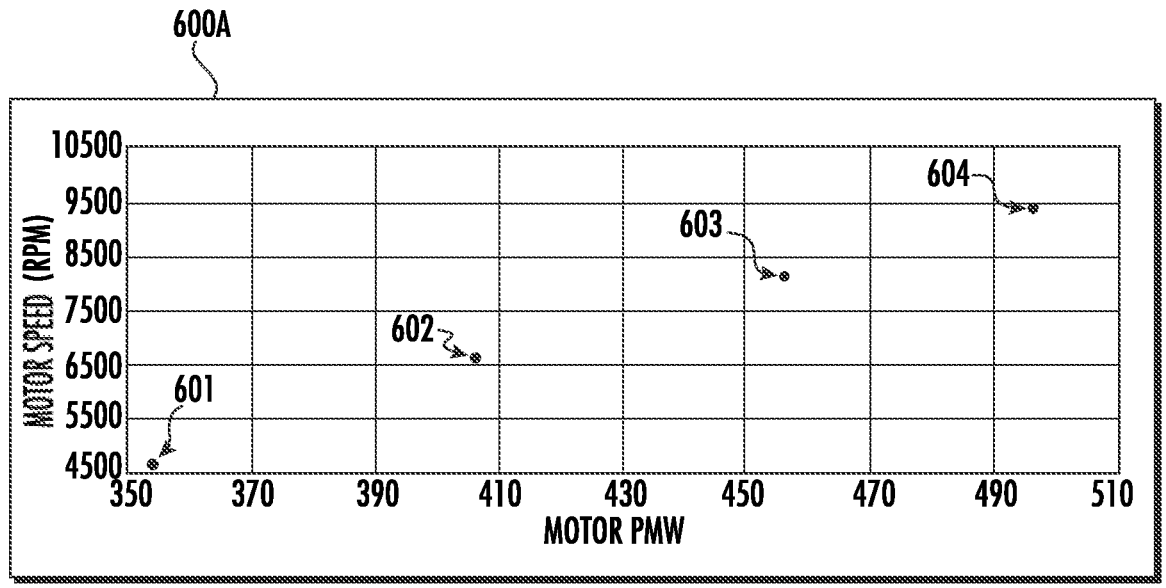
FIGS. 6A-6B illustrate various exemplary graphical representations of exemplary calibrated motor data in accordance with various embodiments.

FIG. 6A illustrates an exemplary graphical representation of exemplary calibrated motor data in accordance with various embodiments. In particular, FIG. 6A shows a graph wherein calibrated motor data is plotted at each of a plurality of motor output calibration points. As illustrated, the exemplary graph 600A is configured to define each of the plurality of calibration points based on the calibrated motor speed data and calibrated motor PWM data associated with each of the plurality of motor output calibration points. As illustrated, the plurality of motor output calibration points comprises four motor output calibration points: a first motor output calibration point 601, a second motor output calibration point 602, a third motor output calibration point 603, and a fourth motor output calibration point 604. The graph 600A is configured such that the calibrated motor PWM values of each motor output calibration point are measured along the x-axis, and the calibrated motor speed values of each motor output calibration point are measured along the y-axis. As such, each motor output calibration point comprises a coordinate in the illustrated x-y plane, wherein the x-component and the y-component of a motor output calibration point are defined by the calibrated motor speed and the calibrated motor PWM, respectively, corresponding to the motor output calibration point. As illustrated, the motor output calibration points 601, 602, 603, 604 are defined according to the exemplary calibrated motor data included above in Table 1.

Returning again to FIG. 4, at Block 403, one or more blower characterization equations may be derived. In various embodiments, a blower characterization equation may define a relationship between various blower motor operating parameters within a blower motor operational range. For example, in various embodiments, a blower characterization equation may be derived in order to define the relationship between the motor speed and the motor voltage for a blower motor operating within a particular blower motor operational range, as described herein. Further, in various embodiments, a derived blower characterization equation may define a relationship between a motor current and a motor voltage within the blower motor operational range. As described herein, wherein a motor output calibration point may correspond to a distinct blower production output, a blower motor operational range may extend between two blower production outputs corresponding, respectively, to two adjacent motor output calibration points, the two adjacent motor output calibration points being relatively adjacent to each other (e.g., sequential) within the plurality of motor output calibration points. For example, a blower motor operational range may be defined at least in part by the plurality of partial blower production outputs between two adjacent motor output calibration points. As described herein, the blower motor operational range in which a blower motor is operating at a particular instance may be determined based at least in part on one or more blower motor operating parameters measured at the particular instance.

As described above, a relationship between various blower motor operating parameters may be determined at each of the plurality of motor output calibration points. Further, in order to determine the relationship between the various blower motor operating parameters at blower production outputs in between calibration points (e.g., within a particular blower motor operational range), one or more blower characterization equations may be derived. In various embodiments, the one or more blower characterization equations may be derived using calibrated motor data. The calibrated motor data at two adjacent motor output calibration points may be used to derive a relationship between various blower motor operating parameters within the blower motor operational range extending between the two adjacent calibration points.

For example, as described above, motor voltage and motor speed may exhibit an at least approximately linear relationship under a constant respirator output flowrate condition. The calibrated motor voltage data and calibrated motor speed data at two adjacent motor output calibration points may be used to derive a particular linear relationship between the motor PWM and the motor speed of a blower motor operating within a blower motor operational range defined by the two adjacent motor output calibration points. Similarly, as described above, motor voltage and motor current may also exhibit an at least approximately linear relationship under a constant respirator output flowrate condition. The calibrated motor voltage data and calibrated motor current data at two adjacent motor output calibration points may be used to derive a particular linear relationship between the motor PWM and the motor speed of a blower motor operating within a blower motor operational range defined by the two adjacent motor output calibration points.

In such exemplary circumstances wherein the relationship between the two blower motor operating parameters is at least substantially linear, the blower characterization equation may be defined by the linear equation form y=mx+b, wherein x and y represent the respective values of the two blower motor operating parameters at a particular instance, m represents the slope of the linear pattern, and b represents a linear constant. For example, in an exemplary circumstance wherein motor voltage is measured along the x-axis and motor speed is measured along the y-axis, the linear constant and the slope of the linear pattern between a first motor output calibration point and a second motor output calibration point (e.g., at a first operational range) may be determined using the equations below:

$$m = \frac{\text{Motor } PMW_{Calibration\ Point\ 2} - \text{Motor } PMW_{Calibration\ Point\ 1}}{\text{Motor } Speed_{Calibration\ Point\ 2} - \text{Motor } Speed_{Calibration\ Point\ 1}}$$

$$b = \text{Motor } Speed_{Calibration\ Point\ 1} - (m * \text{Motor } PMW_{Calibration\ Point\ 1})$$

Figure 6B:
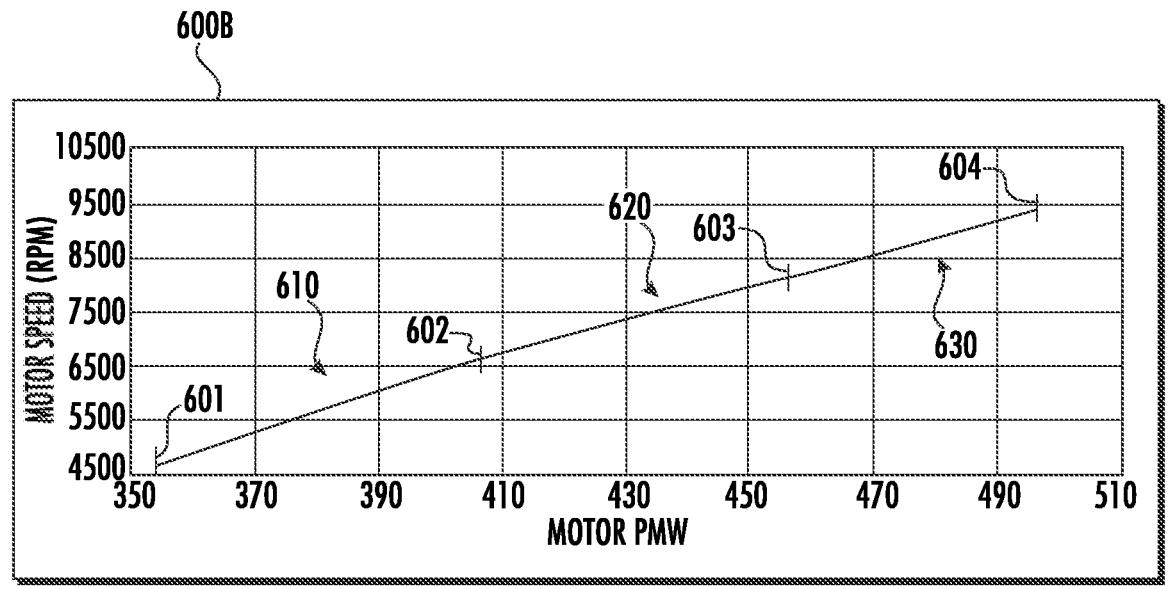

In various embodiments wherein the plurality of motor output calibration points comprises three or more calibration points so as to define a plurality of blower motor operational ranges, one or more blower characterization equations may be derived for each of the plurality of blower motor operational ranges. For example, the exemplary graph 600B illustrated in FIG. 6B is configured to illustrate a relationship between a calibrated motor speed and a calibrated motor PWM of an exemplary blower motor across a plurality of blower motor operational ranges, described above with respect to FIG. 6A. As illustrated in FIG. 6B, in an exemplary circumstance wherein the plurality of motor output calibration points comprises motor output calibration points, 601, 602, 603, 604, the plurality of blower motor operational ranges may comprise three blower motor operational ranges. As illustrated, an exemplary first blower motor operational range may extend between the first motor output calibration point 601 and the second motor output calibration point 602; a second blower motor operational range may extend between the second motor output calibration point 602 and the third motor output calibration point 603; and a third blower motor operational range may extend between the third motor output calibration point 603 and the fourth motor output calibration point 604.

By way of a non-limiting example, using the exemplary calibrated motor data described above in reference to Block 402 and included as a non-limiting illustrative example in FIG. 6A, the slope and linear constant values for the first linear relationship 610 of the motor voltage and the motor speed at the first blower motor operational range (e.g., between a first motor output calibration point 601 and the second motor output calibration point 602) may be:

$$m = \frac{\text{Motor } Voltage_{Calibration\ Point\ 2} - \text{Motor } Voltage_{Calibration\ Point\ 2}}{\text{Motor } Speed_{Calibration\ Point\ 2} - \text{Motor } Speed_{Calibration\ Point\ 1}} = 37.34$$

-continued $$b = 4667 - (37.34 * 354) = -8551$$

Accordingly, the exemplary derived blower characterization equation for a blower motor exhibiting a blower production output between 0 mm H₂O and 22 mm H₂O (e.g., within the first blower motor operational range), illustrated as a first blower characterization curve portion 610, may be:

Motor Speed=(37.34*Motor *PMW*)−8551

Further, using the same exemplary calibrated motor data referenced above, the slope and linear constant values for the linear relationship of the motor voltage and the motor speed at the second blower motor operational range (e.g., between the second motor output calibration point 602 and the third motor output calibration point 603) may be 30.31 and −5710, respectively. Accordingly, the exemplary derived blower characterization equation for a blower motor exhibiting a blower production output between 23 mm H₂O and 46 mm H₂O (e.g., within the second blower motor operational range), illustrated as a second blower characterization curve portion 620, may be:

Motor Speed=(30.31*Motor *PMW*)−5710

Further, using the same exemplary calibrated motor data referenced above, the slope and linear constant values for the linear relationship of the motor voltage and the motor speed at the third blower motor operational range (e.g., between the third motor output calibration point 603 and the fourth motor output calibration point 604) may be 31.85 and −6414, respectively. Accordingly, the exemplary derived blower characterization equation for a blower motor exhibiting a blower production output between 47 mm H₂O and 68 mm H₂O (e.g., within the third blower motor operational range), illustrated as a third blower characterization curve portion 630, may be:

Motor Speed=(31.85*Motor *PMW*)−6414

As illustrated in FIG. 6B, a plurality of derived blower characterization equations corresponding, respectively, to a plurality of blower motor operational ranges may collectively define the relationship between two blower motor operating parameters under a constant respirator output airflow for the full blower motor operational range. Although described herein with respect to various linear relationships, it should be understood that a blower characterization equation may also be derived to define any applicable type of nonlinear relationship between two blower motor operating parameters. In various embodiments, each of the one or more derived blower motor equations may be stored as calibrated motor data associated with a respective operational range that may be selectively retrieved according to one or more operations described in further detail herein.

At Block 404, blower motor data comprising motor speed data, motor voltage data, and motor current data may be generated. In various embodiments, for example, generating blower motor data comprises measuring a motor PWM (e.g., motor voltage) value, motor speed value, and motor current value at a first instance. As described herein, the motor PWM (e.g., motor voltage), the motor speed, and the motor current of an exemplary blower motor may be dynamically measured at one or more instances using an exemplary respirator apparatus in order to characterize, at least in part, the operating state of the blower motor at the first instance. For example, the generated blower motor data may comprise measured motor PWM data, measured motor speed data, and measured motor current data that is collected by one or more measurement devices (e.g., sensors) in electronic communication with an exemplary respirator, as described herein. In various embodiments, as described herein, the generated blower motor data may be associated with an indicator (e.g., an electronic timestamp, and/or the like) relating the data to the first instance. The generated blower motor data may be stored as blower motor data associated with the first instance that may be selectively retrieved according to one or more operations described in further detail herein. For example, the blower motor data associated with the first instance may comprise a first measured motor PWM, a first measured motor speed, and/or a first measured motor current.

Upon generating blower motor data associated with the first instance, method 400 continues at Block 405, a first optimized motor speed of the blower motor at the first instance may be programmatically determined based at least in part on the blower motor data and the one or more blower characterization equation corresponding to a determined blower motor operational range at the first instance. An exemplary method by which such an optimized motor speed may be calculated is shown in FIG. 7, which shows a flowchart illustrating an exemplary method 700 for utilizing blower motor data and a derived blower characterization equation to programmatically determine an optimized motor speed.

Figure 7:
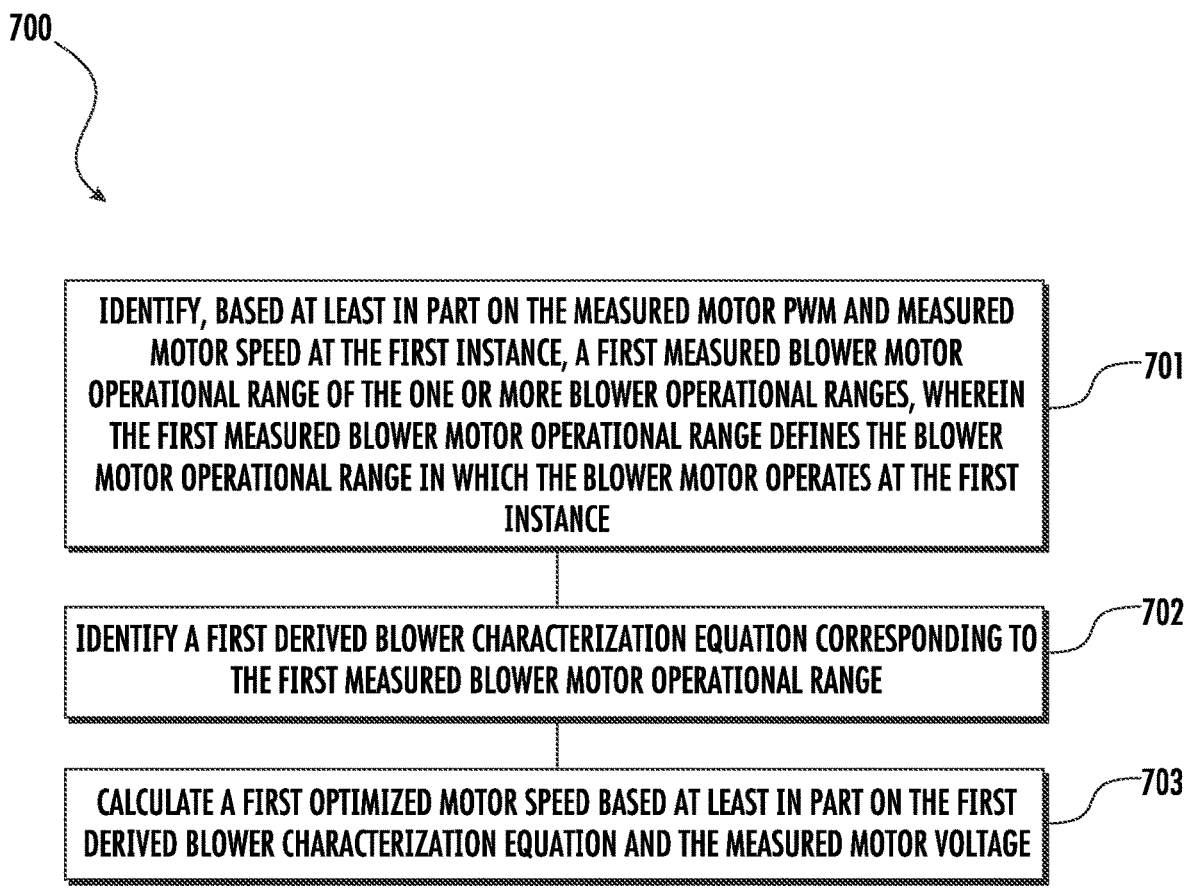
FIG. 7 is a flowchart illustrating example steps for programmatically determining an optimized motor speed in accordance with various embodiments.

As shown at Block 701 of FIG. 7, a first measured blower motor operational range of the one or more blower operational ranges may be identified. As described herein, the first measured blower motor operational range may comprise the blower motor operational range in which the blower motor was operating at the first instance. Wherein each blower motor operational range may correspond to a respective blower characterization equation, the first measured blower motor operational range may be identified in order to determine which of the one or more blower characterization equations most accurately characterizes the operating state of the blower motor at the first instance, and thus, which of the one or more blower characterization equations should be used to determine the first optimized motor speed of the blower motor at said first instance. In various embodiments, the first measured blower motor operational range may be identified based at least in part on the generated blower motor data associated with the first instance, such as, for example, the motor PWM and/or the motor speed of the blower motor measured at the first instance. As described above in reference to FIGS. 6A-6B, each of the blower motor operational ranges may be defined by adjacent motor output calibration points at which respective calibrated motor data (e.g., calibrated motor voltage data, calibrated motor speed data, etc.) has been calculated. For example, the value of the measured motor PWM at the first instance (e.g., the first measured motor PWM) may be determined to fall within the two calibrated motor PWMs of adjacent motor output calibration points. A first measured blower motor operational range may be identified as the blower motor operational range defined by the two adjacent motor output calibration points associated, respectively, with the two calibrated motor PWMs between which the measured motor PWM falls. As an illustrative, non-limiting example, using the exemplary calibrated motor data described above in reference to Block 402 and included as a non-limiting illustrative example in reference to FIGS. 6A-6B, the four exemplary calibration points may correspond to calibrated motor PWMs of 354, 404, 456, and 496, respectively. For example, in an exemplary circumstance wherein the measured motor PWM at the first instance has a value of 410, the blower motor operational range in which the blower motor was operating at the first instance (e.g., the first measured blower motor operational range) may be identified as the blower motor operational range that is defined by the second motor output calibration point and the third motor output calibration point. As such, the second blower motor operational range, as defined above, may be identified as the first measured blower motor operational range, indicating that it may be estimated that the blower motor was exhibiting a blower production output of between 23 mm $H_2O$ and 46 mm $H_2O$ at the first instance.

Upon identifying the first measured blower motor operational range, at Block 702, a first derived blower motor characterization equation may be identified. As described above, a derived blower motor characterization equation may comprise an equation derived to define a relationship between various blower motor operating parameters (e.g., motor PWM and motor speed) within a blower motor operational range. For example, the first derived blower motor characterization equation may comprise the derived blower motor characterization equation corresponding to the first measured blower motor operational range. That is, the first derived blower motor characterization equation may comprise an equation derived to define a relationship between various blower motor operating parameters (e.g., motor PWM and motor speed) within the first measured blower motor operational range. For example, in various embodiments, identifying a first derived blower characterization equation may comprise retrieving stored calibrated motor data comprising at least one of the one or more derived blower characterization equation. Continuing the illustrative exemplary described above, the derived blower characterization equation may be identified as the derived blower characterization equation corresponding to the second blower motor operational range (e.g., the blower motor operational range defined by a blower production output of between 23 mm $H_2O$ and 46 mm $H_2O$). In such an exemplary circumstance, the first derived blower characterization equation may be identified as Motor Speed=(30.31*Motor PMW)−5710.

Upon identifying the first measured blower motor operational range, exemplary method 700 may continue at Block 703, with calculating a first optimized motor speed. In various embodiments, the first optimized motor speed may be defined as a motor speed at which an exemplary blower motor operating at a known motor voltage (e.g., the measured motor voltage at the first instance) should be operating in order to produce a desired respirator output flowrate. In various embodiments, the first optimized motor speed may be calculated using the first derived blower characterization equation and the blower motor data associated with the first instance. In various embodiments, calculating the first optimized motor speed may comprise retrieving stored calibrated motor data and/or stored blower motor data associated with the first instance. For example, at least a portion of the blower motor data (e.g., measured motor voltage data) associated with the first instance may be used as an input into the first derived blower motor characterization equation, which corresponds to the blower motor operational range in which the blower motor was operating at the first instance (e.g., the first measured blower motor operational range) in order to determine the first optimized motor speed. Continuing the illustrative exemplary described above, the first derived blower calibration equation may be manipulated to reflect the measured motor PWM associated the first instance. In the exemplary circumstance referenced above wherein the measured motor PWM at the first instance is measured as 410, the first derived blower calibration equation may be manipulated to read as follows: Motor Speed= (30.31*410)−5710. Accordingly, the first optimized motor speed of the blower motor may be programmatically determined to be 6,717.10 RPM.

With reference again to FIG. 4, method 400 may continue with adjusting the first measured motor speed based at least in part on measured temperature data associated with the first instance, as shown at Block 406. The output flow rate of a respirator within an ambient environment may be affected by one or more ambient environment conditions, such as, for example, ambient temperature. In various embodiments, the motor speed of a blower motor may be directly proportional to the ambient temperature of the ambient environment in which the blower motor is operating. For example, in various embodiments, a change in ambient temperature may result in a change in motor speed without a corresponding proportional change in respirator output flowrate. In such an exemplary circumstance, the above-described relationship between motor speed and respirator output flowrate may deviate from an approximately linear relationship such that the motor speed of a blower motor at a given instance may not function as an accurate indicator of the respirator output flowrate. Further, in various embodiments, the motor current and respirator output flowrate may remain at least substantially the same through changes in temperature. As described herein, the first measured motor speed of an exemplary blower motor may be programmatically adjusted in order to compensate for the effect of ambient temperature on the production output of the blower motor. For example, a measured motor speed may be adjusted to determine an adjusted measured motor speed, the adjusted measured motor speed comprising a motor speed value wherein the increase/decrease in motor speed caused by the ambient temperature, which was reflected in the measured motor speed, has been programmatically removed.

In various embodiments, in order to maintain a substantially consistent respirator output flowrate, the measured ambient temperature at a first instance may be accounted for by programmatically adjusting the first measured motor speed of an exemplary blower motor using a motor speed temperature compensation factor to determine a first adjusted measured motor speed. As described above, the motor speed of a blower motor may be directly proportional to the ambient temperature of the ambient environment in which the blower motor is operating. For example, as the ambient temperature increases, the motor speed of the blower motor also increases due at least in part to the effect of the varying temperature on the resistance of the blower motor's motor coil. Further, in various embodiments, the motor coil resistance of an exemplary blower motor may correspond, at least in part, to the back electromagnetic force (EMF) of the blower motor. For example, the back EMF of a blower motor may be directly proportional to the motor speed of the blower motor. Accordingly, in various embodiments, the effect of an ambient temperature on one or more blower motor operating parameters (e.g., motor speed) of a blower motor may be determined based at least in part on the change in back EMF of the blower motor caused by the ambient temperature. In various embodiments, the back EMF may be measured by the difference between a measured motor voltage and the product of the motor coil resistance and a measured motor current, as shown in the following equation:

Back $EMF$=Motor Voltage−(Motor Current*Motor Coil Resistance)

In various embodiments, the motor coil resistance corresponding to a change in ambient temperature relative to a reference temperature may be defined by the following equation:

$R_{coil} = R_{Coil,Reference}(1+\text{Temperature Coefficient}_{coil}(T_{Current}-T_{Reference}))$ Accordingly, a first back EMF (e.g., the back EMF calculated at a first measured temperature) may comprise the difference between a first measured motor voltage (e.g., the motor voltage measured at the first instance) and the product of the motor coil resistance and the first measured motor current (e.g., the motor current measured at the first instance), as described above. Further, the change in back EMF of the blower motor may be defined by the difference between the first back EMF calculated at a first measured temperature (e.g., the ambient temperature measured at the first instance) and a reference back EMF value calculated at a reference temperature value, such as, for example, 24 degrees Celsius. In various embodiments, a motor speed temperature compensation factor, a value which may be applied to the first measured speed in order to compensate for an ambient temperature, as described herein, may be determined by dividing the change in back EMF of the blower motor by a back EMF constant. For example, in various embodiments, the value of the back emf constant may comprise stored blower motor data which may be retrieved in order to calculate a motor speed temperature compensation factor. In various embodiments, the adjusted measured motor speed may be determined by subtracting a motor speed temperature compensation factor from the measured motor speed, as illustrated in the equation below:

Motor Speed$_{Adjusted}$

=Motor Speed$_{Measured}$

−Compensation Factor$_{Motor\ Speed,Temperature}$

Accordingly, the first adjusted measured motor speed may be defined by the difference between the first measured motor speed and the calculated first motor speed temperature compensation factor. As described herein, the first adjusted measured motor speed may comprise a motor speed value wherein the increase/decrease in motor speed caused by the first measured temperature, which was reflected in the first measured motor speed, has been programmatically removed. In various embodiments, the invention described herein may be configured to be able to maintain operability and the increased accuracy described herein in ambient environments having an ambient temperature of at least substantially between −20° C. and 65° C. (e.g., between −10° C. and 55° C.).

At Block 407, the first measured motor speed may be adjusted based at least in part on measured ambient pressure data associated with the first instance. As described herein, in various embodiments, the output flow rate of an exemplary respirator within an ambient environment may be affected by one or more ambient environment conditions, such as, for example, an altitude at which the respirator is operating. In various embodiments, the motor speed of the blower motor may be effected by the altitude at which the respirator is operating. For example, variations in altitude may correlate to changes in the atmospheric pressure of an ambient environment. In various embodiments, as the altitude of an ambient environment increases, the atmospheric pressure of the environment may decrease proportionately. Further, the motor speed of the blower motor may be inversely proportional to the atmospheric pressure of the ambient environment in which the respirator is operating. A decrease in ambient pressure causes the load condition acting on the impeller of the blower motor to decrease, resulting in an increased motor speed of the blower motor. Accordingly, an increase in altitude may result in an increased motor speed that does not correlate to a proportional increase in respirator output flowrate. A change in altitude resulting in a corresponding change motor speed without a proportional change in respirator output flowrate causes the relationship between the motor speed and the respirator output flowrate at a particular instance to deviate from its aforementioned approximately linear relationship such that the motor speed of a blower motor at a given instance may not function as an accurate indicator of the respirator output flowrate at that instance. Further, in various embodiments, the motor current may remain at least substantially the same (e.g., negligible motor current variances) through changes in altitude. As described herein, the first measured motor speed of an exemplary blower motor may be programmatically adjusted in order to compensate for the effect of altitude (e.g., ambient pressure) on the production output of the blower motor. For example, a measured motor speed may be adjusted to determine an adjusted measured motor speed, the adjusted measured motor speed comprising a motor speed value wherein the increase/decrease in motor speed caused by the altitude (e.g., ambient pressure), which was reflected in the measured motor speed, has been programmatically removed.

In various embodiments, in order to maintain a substantially consistent respirator output flowrate, the measured ambient pressure at a first instance may be accounted for by programmatically adjusting the first measured motor speed of an exemplary blower motor using a motor speed pressure compensation factor to determine a first adjusted measured motor speed. As described above, the motor speed of a blower motor may be inversely proportional to the atmospheric pressure of the ambient environment in which the respirator is operating. For example, as the altitude of an exemplary respirator increases and, accordingly, the ambient pressure proportionately decreases, the motor speed of the blower motor may increase due at least in part to a decreased pressure load acting on the impeller of the blower motor. In various embodiments, a motor speed pressure compensation factor, a value which may be applied to the first measured speed in order to compensate for an ambient pressure (e.g., an altitude), as described herein, may be determined using a derived regression equation that considers a measured ambient pressure and various blower motor data. For example, experimental data comprising blower motor data (e.g., motor speed data) generated over a range of different ambient pressures may be used to programmatically derive a regression equation through which a motor speed pressure compensation factor may be determined. As an illustrative and non-limiting example, a motor speed pressure compensation factor may be determined using the following equation derived for an exemplary blower motor configuration, which correlates the motor speed pressure compensation factor to a change in ambient pressure ($\Delta Pressure_{Ambient}$) (e.g., between a measured ambient pressure and a reference ambient pressure) and/or a change in motor PWM ($\Delta$Motor PWM):

Compensation Factor$_{Motor\ Speed,Pressure}$ $$=-360.98+1.7678(\Delta \text{Motor } PWM)+5.0553$$
$$(\Delta \text{Pressure}_{Ambient})$$

$$-0.00214(\Delta \text{Motor } PWM^2)+0.00306$$
$$(\Delta \text{Pressure}_{Ambient}^2)$$

$$-0.019031(\Delta \text{Motor } PWM * \Delta \text{Pressure}_{Ambient})$$

For example, in order to identify a motor speed pressure compensation factor in an exemplary circumstance wherein the motor PWM remains unchanged, the above equation may be represented as follows:

$$\text{Compensation Factor}_{Motor\ Speed,Pressure}$$

$$=-360.98+5.0553(\Delta \text{Pressure}_{Ambient})$$

$$+0.00306(\Delta \text{Pressure}_{Ambient}^2)$$

In various embodiments, the adjusted measured motor speed may be determined by subtracting a motor speed pressure compensation factor from the measured motor speed, as illustrated in the equation below:

$$\text{Motor Speed}_{Adjusted}$$

$$=\text{Motor Speed}_{Measured}-\text{Compensation Factor}_{Motor\ Speed,Pressure}$$

Accordingly, the first adjusted measured motor speed may be defined by the difference between the first measured motor speed and the calculated first motor speed pressure compensation factor. As described herein, the first adjusted measured motor speed may comprise a motor speed value wherein the increase/decrease in motor speed caused by the first measured pressure (e.g., a first altitude), which was reflected in the first measured motor speed, has been programmatically removed. In various embodiments, the invention described herein may be configured to be able to maintain operability and the increased accuracy described herein in ambient environments having ambient altitude variations of at least substantially between 0 feet and 12000 feet (e.g., between 0 feet and 8000 feet). For example, in such an exemplary circumstance, the invention described herein may be configured to be able to maintain operability and the increased accuracy described herein in ambient environments having ambient pressure of at least substantially between 101300 Pa and 65000 Pa (e.g., between 101300 Pa and 75000 Pa).

In various embodiments, the first measured motor speed of an exemplary blower motor may be programmatically adjusted in order to compensate for both the effect of altitude (e.g., ambient pressure) and the effect of ambient temperature on the production output of the blower motor. For example, a measured motor speed may be adjusted to determine an adjusted measured motor speed that represents a motor speed value wherein the increase/decrease in motor speed caused by an ambient altitude (e.g., ambient pressure) and the increase/decrease in motor speed caused by the ambient temperature, both of which are reflected in the measured motor speed, have each been programmatically removed. In such an exemplary circumstance, the adjusted measured motor speed may be determined by subtracting a motor speed pressure compensation factor from the measured motor speed, as illustrated in the equations below:

$$\text{Motor Speed}_{Adjusted}$$

$$=\text{Motor Speed}_{Measured}-\text{Compensation Factor}_{Motor\ Speed,Pressure}$$

$$-\text{Compensation Factor}_{Motor\ Speed,Temperature}$$

Accordingly, the first adjusted measured motor speed may be defined by the difference between the first measured motor speed and a cumulative first motor speed compensation factor, defined as the combination of the first motor speed temperature compensation factor and the first motor speed pressure compensation factor. As described herein, the first adjusted measured motor speed may comprise a motor speed value wherein the increase/decrease in motor speed caused by the first measured temperature and the first measure altitude (e.g., pressure), which were both reflected in the first measured motor speed, have been programmatically removed.

At Block 408, the first adjusted measured motor speed and the first optimized motor speed may be compared. As described herein, in various embodiments, the first optimized motor speed may represent the motor speed at which the exemplary blower motor should be operating in order to produce the desired respirator output flowrate, given the first measured motor PWM. Accordingly, the first adjusted measured motor speed may be compared to the first optimized motor speed in order to approximate whether or not the respirator output flowrate being driven by the exemplary blower motor at the first instance (e.g., the first respirator output flowrate) is at least substantially consistent with the desired respirator output flowrate. For example, comparing the first adjusted measured motor speed to the first optimized motor speed may comprise determining a difference between the first adjusted measured motor speed and the first optimized motor speed. In various embodiments, the difference between the first adjusted measured motor speed and the first optimized motor speed may be analyzed in order to determine whether the first adjusted measured motor speed falls within an acceptable measured motor speed tolerance range. For example, the acceptable measured motor speed tolerance range may comprise a range of motor speed values centered about an optimized motor speed at a particular instance. In various embodiments, the acceptable measured motor speed tolerance range may be configured such that an adjusted measured motor speed determined to fall within the acceptable measured motor speed tolerance range at an instance (e.g., within 20 RPM of the optimized motor speed at that instance) may correspond to a blower motor that is producing a respirator output flowrate that is within an acceptable respirator output flowrate tolerance range. As described herein, an acceptable respirator output flowrate tolerance range may comprise a range of at least substantially consistent respirator output flowrate values centered about a desired respirator output flowrate. Accordingly, the first adjusted measured motor speed and the first optimized motor speed may be compared in order to determine whether the first adjusted measured motor speed falls within the acceptable measured motor speed tolerance range, such that, at the first instance, the blower motor is producing a first respirator output flowrate that is at least substantially consistent with the desired respirator output flowrate.

At Block 409, the first adjusted measured motor speed may be identified as being within an acceptable measured motor speed tolerance range. In various embodiments, wherein the difference between the first adjusted measured motor speed and the first optimized motor speed is such that the first adjusted measured motor speed falls within the acceptable measured motor speed tolerance range, it may be estimated that a first respirator output flowrate (e.g., the respirator output flowrate driven by the blower motor at the first instance is within an acceptable respirator output flowrate tolerance range. For example, in such an exemplary circumstance wherein the first adjusted measured motor speed falls within the acceptable measured motor speed tolerance range, the relationship between the first adjusted measured motor speed and the first measured motor PMW (e.g., the relationship between the adjusted measured motor speed and the measured motor PMW at the first instance) may be at least substantially similar to the exemplary relationship defined by the calibrated motor data and the blower characterization equation corresponding to blower motor operational range of the blower motor at the first instance, as described herein. Accordingly, as described herein, wherein the first adjusted measured motor speed is identified as falling within acceptable measured motor speed tolerance range, the first respirator output flowrate (e.g., the respirator output flowrate driven by the blower motor at the first instance) is determined to be at least substantially consistent with the desired respirator output flowrate.

As an illustrative and non-limiting example, the acceptable measured motor speed tolerance range may comprise a range of motor speed values extending at least approximately 20 RPM above and below an optimized motor speed. In such an exemplary circumstance, a motor speed (e.g., an adjusted measured motor speed) measured at a given instance that is within 20 RPM of an optimized motor speed calculated for that instance falls within the acceptable measured motor speed tolerance range. In various embodiments, an acceptable respirator output flowrate tolerance range may be defined, at least in part, by an upper respirator output flowrate limit and a lower respirator output flowrate limit, wherein the acceptable respirator output flowrate tolerance range comprises a range of respirator output flowrate values that are less than or equal to an upper respirator output flowrate limit and greater than or equal to a lower respirator output flowrate limit. As a non-limiting example, the upper respirator output flowrate limit and the lower respirator output flowrate limit of an acceptable respirator output flowrate tolerance range may be 15 liters per minute more than the desired respirator output flowrate and less than the desired respirator output flowrate, respectively. In such and exemplary circumstance, wherein a desired respirator output flowrate is 190 LPM, the acceptable respirator output flowrate tolerance range comprises a range of respirator output flowrate values between 175 LPM and 205 LPM. In various embodiments, an exemplary method in which the respirator output flowrate is maintained using an acceptable measured motor speed tolerance range and an acceptable respirator output flowrate tolerance range defined by such exemplary values, as well as a blower characterization curve defined by four motor output calibration points, as described herein, may correspond to a process that is capable of operating so as to produce approximately 188 defects per million opportunities. For example, a defect may be defined as a respirator output airflow that falls outside of the acceptable respirator output flowrate tolerance range. Such an exemplary process may comprise a 4.5 sigma capable process.

In various embodiments wherein the first respirator output flowrate is at least substantially consistent with the desired respirator output flowrate, it may be determined that the one or more blower motor operating parameters should not be programmatically adjusted in order to incite a corresponding change in the respirator output flowrate of the blower motor. In such a circumstance, a method of producing an at least substantially consistent respirator output flowrate may be continued by repeating at least a portion of the operations described herein in reference to Blocks 404-409. For example, as illustrated in FIG. 4, exemplary method 400 may continue by generating blower motor data comprising, for example, motor voltage data, motor speed data, and motor current data associated with a second instance, wherein the second instance comprises a moment in time that is sequentially after the first instance. As described herein, blower motor data associated with the second instance may be generated by dynamically measuring, for example, a second measured motor PWM, a second measured motor speed, and a second measured motor current (e.g., the motor PWM, motor speed, and motor current measured at the second instance). In various embodiments, at least a portion of the steps of exemplary method 400 described herein in reference to Blocks 404-409 may be repeated at least once (e.g., in perpetuity) in order to ensure that the respirator output flowrate is remains at least substantially consistent over time.

Referring back to Block 408, the exemplary method 400 may continue at Block 410, with identifying that the first adjusted measured motor speed is not within an acceptable measured motor speed tolerance range. In various embodiments, wherein the difference between the first adjusted measured motor speed and the first optimized motor speed is such that the first adjusted measured motor speed falls outside of the acceptable measured motor speed tolerance range, it may be estimated that the first respirator output flowrate is not within an acceptable respirator output flowrate tolerance range. For example, in such an exemplary circumstance wherein the first adjusted measured motor speed falls outside of the acceptable measured motor speed tolerance range, the relationship between the first adjusted measured motor speed and the first measured motor PMW may deviate from the exemplary relationship defined by the calibrated motor data and the first measured blower characterization equation. Accordingly, wherein the first adjusted measured motor speed is identified as falling outside of the acceptable measured motor speed tolerance range, the first respirator output flowrate (e.g., the respirator output flowrate driven by the blower motor at the first instance) is determined to be undesirably inconsistent with the desired respirator output flowrate. In various embodiments wherein the first respirator output flowrate is not at least substantially consistent with the desired respirator output flowrate, it may be determined that one or more blower motor operating parameters may be programmatically adjusted in order to incite a corresponding change in the respirator output flowrate of the blower motor.

In various embodiments, upon identifying that the first adjusted measured motor speed is not within an acceptable measured motor speed tolerance range, the exemplary method 400, may continue at Block 411 with programmatically adjusting the first measured motor voltage. The first measured motor voltage may be programmatically adjusted by selectively adjusting the first measured motor PWM, as described herein. For example, the first measured motor PWM may be programmatically adjusted in order to configure the blower motor (e.g., one or more blower motor operating parameters) to produce a respirator output flowrate that is at least substantially consistent with the desired respirator output flowrate, as described herein. In various embodiments, wherein the first adjusted measured motor speed of the blower motor is identified as being greater than the acceptable measured motor speed tolerance range at the first instance, the first respirator output flowrate produced by the blower motor may be undesirably low. For example, such an undesirably low flow rate may be caused by one or more respirator operational conditions, such as, for example, a blockage of the respirator air flow path caused by an at least partially clogged filter assembly, causing the first respirator output flowrate to be less than the lower respirator output flowrate limit, as described herein. Further, wherein the first adjusted measured motor speed is identified as being less than the acceptable measured motor speed tolerance range at the first instance, the first respirator output flowrate produced by the blower motor may be undesirably high. For example, the first respirator output flowrate may be greater than the upper respirator output flowrate limit, as described herein. In various embodiments, the first measured motor PWM may be modified such that the respirator output flowrate produced by the blower motor is adjusted to be at least substantially consistent with a desired respirator output flowrate.

For example, in an exemplary circumstance wherein the first measured respirator output flowrate is identified as being undesirably low, the first measured motor PWM of the blower motor may be increased so as to increase the respirator output flowrate produced by the blower motor, as described herein. Further, in an exemplary circumstance wherein the first measured respirator output flowrate is identified as being undesirably high, the first measured motor PWM of the blower motor may be decreased so as to decrease the respirator output flowrate produced by the blower motor, as described herein. In various embodiments, as described herein, the programmatic adjustment of the motor PWM may be based at least in part on the difference between the first adjusted measured motor speed and the first optimized motor speed.

Figure 8:
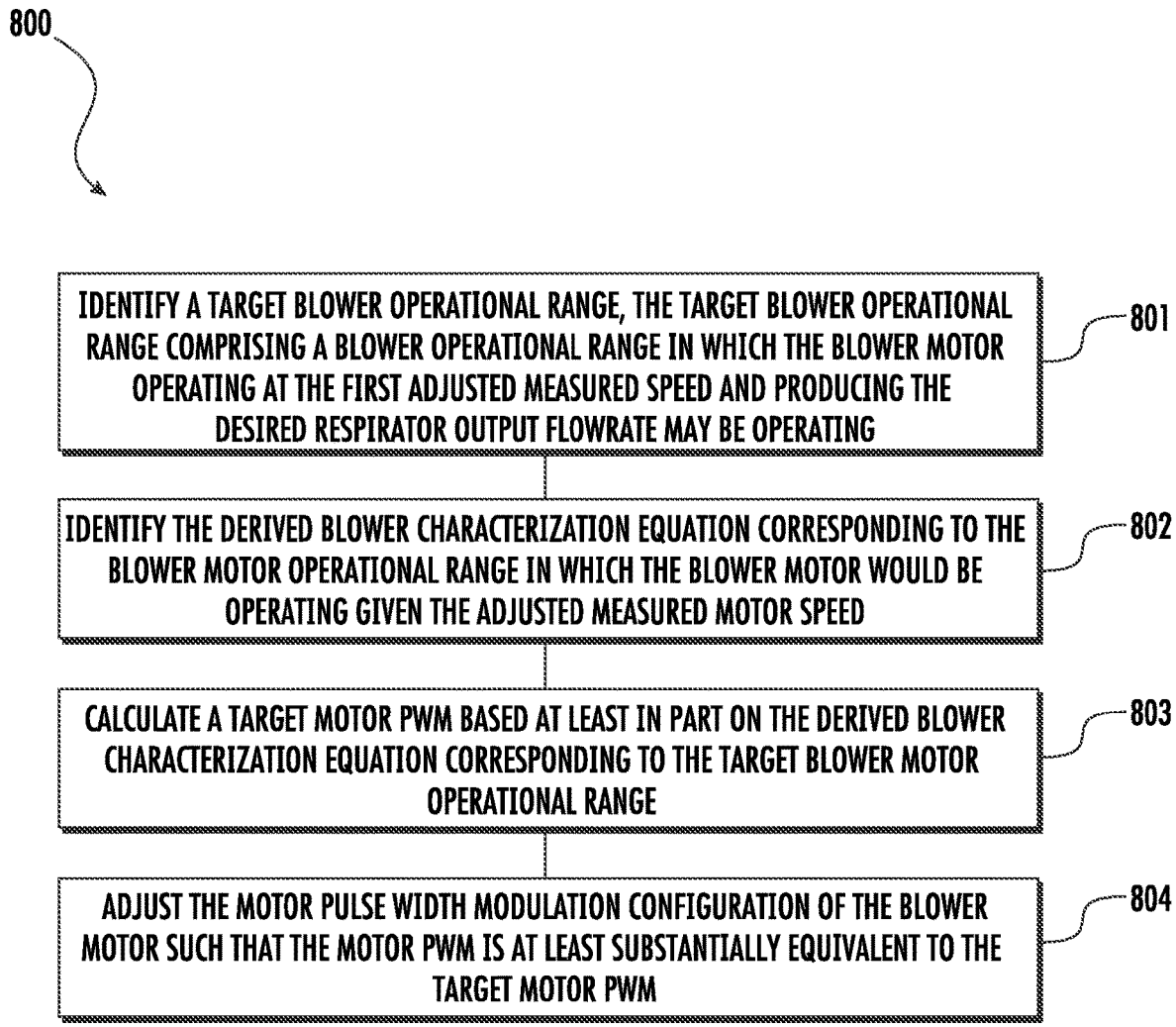
FIG. 8 is a flowchart illustrating example steps for programmatically adjusting motor voltage of an exemplary respirator in accordance with various embodiments.

An exemplary method by which such the first measured motor PWM may be programmatically adjusted is shown in FIG. 8, which shows a flowchart illustrating an exemplary method 800 for adjusting the first measured motor PWM based at least in part on one or more blower characterization equations and the first adjusted measured motor speed. In various embodiments, prior to being programmatically adjusted based on the first adjusted measured motor speed, the blower motor may be configured to operate that motor pulse width modulation configuration comprises a 40% duty cycle "on" time. As shown at Block 801 of FIG. 8, a target blower motor operational range may be identified. In various embodiments, the target blower motor operational range may be defined as the blower motor operational blower range in which an exemplary blower motor may operate in order to produce the desired respirator output flowrate while operating at the first adjusted measured motor speed. As described above in reference to FIGS. 6A-6B, each blower motor operational range may be defined by adjacent motor output calibration points at which respective calibrated motor data (e.g., calibrated motor voltage data, calibrated motor speed data, etc.) has been calculated. For example, the value of the first adjusted measured motor speed may be determined to fall within the two calibrated motor speeds of adjacent motor output calibration points. A target measured blower motor operational range may be identified as the blower motor operational range defined by the two adjacent motor output calibration points associated, respectively, with the two calibrated motor speeds between which the first adjusted measured motor speed falls. As an illustrative, non-limiting example, using the exemplary calibrated motor data described above in reference to Block 402 and included as a non-limiting illustrative example in reference to FIGS. 6A-6B, the four exemplary calibration points may correspond to calibrated motor speeds of 4667, 6534, 8110, and 9384 RPM, respectively. For example, in an exemplary circumstance wherein the first adjusted measured motor speed has a value of 6800 RPM, the target blower motor operational range may be identified as the blower motor operational range that is defined by the second motor output calibration point and the third motor output calibration point. As such, the second blower motor operational range, as defined above, may be identified as the target blower motor operational range, indicating that an exemplary blower motor producing the desired respirator output flowrate and operating at the first adjusted measured motor speed may exhibit a blower production output of between 23 mm $H_2O$ and 46 mm $H_2O$.

Upon identifying the target blower motor operational range, at Block 802, the blower motor characterization equation corresponding to the target blower motor operational range may be identified. For example, in various embodiments, identifying the blower motor characterization equation corresponding to the target blower motor operational range may comprise retrieving stored calibrated motor data comprising at least one of the one or more derived blower characterization equations. Continuing the illustrative exemplary described above, the derived blower characterization equation corresponding to the target blower motor operational range may be identified as the derived blower characterization equation corresponding to the second blower motor operational range (e.g., the blower motor operational range defined by a blower production output of between 23 mm $H_2O$ and 46 mm $H_2O$). In such an exemplary circumstance, the derived blower characterization equation corresponding to the target blower motor operational range may be identified as Motor Speed=(30.31*Motor PMW)−5710. In various embodiments, the derived blower characterization equation corresponding to the target blower motor operational range may be either the same or different than the first derived blower characterization equation, as described above, which corresponds to the first measured blower motor operational range.

Upon identifying the derived blower characterization equation corresponding to the target blower motor operational range, at Block 803, a target motor PWM may be calculated. In various embodiments, the target motor PWM may be defined as a motor PWM value that an exemplary blower motor configured as described herein and operating at a known motor speed (e.g., the first adjusted measured motor speed) should exhibit in order to produce a desired respirator output flowrate. In various embodiments, the target motor PWM may be calculated using the derived blower characterization equation corresponding to the target blower motor operational range and the first adjusted measured motor speed. In various embodiments, calculating the target motor PWM may comprise retrieving stored calibrated motor data and/or stored blower motor data associated with the first instance. For example, at least a portion of the blower motor data associated with the first instance (e.g., the first adjusted measured motor speed) may be used as an input into the derived blower characterization equation corresponding to the target blower motor operational range in order to determine the target motor PWM. Continuing the illustrative exemplary described above, the derived blower characterization equation corresponding to the target blower motor operational range may be manipulated to reflect the first adjusted measured motor speed. In the exemplary circumstance referenced above wherein the first adjusted measured motor speed is determined to be 6800 RPM, the first derived blower calibration equation may be manipulated to read as follows: Target Motor PWM=(6800+5710)/30.31. Accordingly, the target motor PWM of the blower motor may be programmatically determined to be 412.735.

Upon calculating the target motor PWM, exemplary method 800 may continue at Block 804, with programmatically adjusting the motor pulse width modulation configuration of the blower motor such that the motor PWM is at least substantially equivalent to the target motor PWM. In various embodiments, the pulse width modulation configuration of a blower motor may be defined at least in part by the motor PWM of the blower motor, which may be defined by the duty cycle count of a PWM voltage signal, as described herein. For example, each duty cycle count of the pulse width modulation configuration may correspond to an incremental voltage step that corresponds to a fraction of the maximum motor voltage of the blower motor. As such, a change in the motor PWM corresponds to a change in the duty cycle count of the blower motor, which may incite a corresponding variation in the motor voltage exhibited by the blower motor. As a non-limiting illustrative example, the motor voltage of the blower motor having a known maximum motor voltage of 10 volts may be selectively varied using a PWM voltage signal comprising 250 steps. Accordingly, each of the 250 steps of the exemplary PWM voltage signal may be associated with a respective duty cycle count that corresponds to a motor voltage of 0.04 volts. For example, by selectively increasing the motor PWM of the exemplary blower motor by 10 counts, the motor voltage of the blower motor may be increased by 0.4 volts.

As described herein, programmatically adjusting the motor pulse width modulation configuration of a blower motor may comprise selectively adjusting the motor PWM so as to adjust the motor speed of the blower motor, and thus, the respirator output flowrate produced by the blower motor. In various embodiments, programmatically adjusting the motor pulse width modulation configuration of a blower motor such that the motor PWM is at least substantially equivalent to the target motor PWM may comprise selectively changing the motor PWM of the blower motor from the first measured motor PWM to the target motor PWM. For example, by selectively changing the motor PWM of the blower motor from the first measured motor PWM to the target motor PWM, the motor voltage of the blower motor may be adjusted. In various embodiments, as described herein, the variation of the motor voltage caused by the adjustment of the motor PWM may cause the motor speed of the blower motor to undergo a proportional change. For example, in an exemplary circumstance wherein the adjustment of the motor PWM from the first measured motor PWM to the target motor PWM comprises an increase in motor PWM, the motor speed of the blower motor may also be increased. In various embodiments, the increased motor speed resulting from the selectively increased motor PMW may correspond to an increase in the respirator output flowrate driven by the blower assembly (e.g., the blower motor). Accordingly, as described herein, the motor PWM may be programmatically adjusted in order to adjust the motor speed of the blower motor such that the respirator output flowrate may remain at least substantially consistent with a desired respirator output flowrate.

As a further non-limiting example of a method by which such the first measured motor PWM may be programmatically adjusted, in various embodiments, the programmatic adjustment of the motor PWM may be based at least in part on the difference between the first optimized motor speed and the first adjusted measured motor speed (e.g., first motor speed deviation). For example, a first motor speed deviation (e.g., a difference between the optimized motor speed and the measured motor speed at a first instance) may be defined by the following equation: First Motor Speed Deviation=((First Optimized Motor Speed)−(First Adjusted Measured Motor Speed)). In various embodiments, the motor PWM may be programmatically adjusted by a number of counts corresponding to, for example, the first motor speed deviation divided by a value of 10 (e.g., (First Motor Speed Deviation/10) counts). In various embodiments, as described herein, the motor speed deviation may be divided by a value that is defined based on a duty cycle count determined to correspond to a predetermined change in respirator output flowrate. For example, in various embodiments, it may be determined that adjusting the motor speed by a motor PWM count of at least approximately 10 may correspond to a 1 LPM change in respirator output flowrate.

Additionally, or alternatively, the first measured motor PWM may be programmatically adjusted based at least in part on the difference between a first optimized motor current and the first measured motor current (e.g., first motor current deviation). For example, a first motor current deviation (e.g., a difference between the optimized motor current and the measured motor current at a first instance) may be defined by the following equation: First Motor Current Deviation=((First Optimized Motor Current)−(First Measured Motor Current)). In various embodiments, the motor PWM may be programmatically adjusted by a number of counts corresponding to, for example, the first motor current deviation divided by a value of 50 (e.g., (First Motor Current Deviation/50) counts). In various embodiments, as described herein, the motor current deviation may be divided by a value that is defined based on a duty cycle count determined to correspond to a predetermined change in respirator output flowrate. For example, in various embodiments, it may be determined that adjusting the motor current by a motor PWM count of at least approximately 50 may correspond to a 1 LPM change in respirator output flowrate.

Further, in various embodiments, an exemplary method may comprise programmatically adjusting the motor PWM may comprise determining whether the first motor speed deviation (e.g., the difference between the first optimized motor speed and the first adjusted measured motor speed) is larger than the first motor current deviation (e.g., the difference between the first optimized motor current and the first measured motor current). For example, in an exemplary circumstance wherein respirator flow output has increased, the motor PWM will need to be programmatically decreased to reduce the respirator output flow. In such an exemplary circumstance, and wherein the first motor speed deviation is determined to be larger than the first motor current deviation, the motor PWM may be programmatically adjusted to realize a new motor PWM value (e.g., a second measured motor PWM) by the following equation: New Motor PWM=First Measured PWM−(First Motor Speed Deviation/ 10). Further, in an exemplary circumstance wherein respirator flow output has increased and wherein the first motor current deviation is determined to be larger than the first motor speed deviation, the motor PWM may be programmatically adjusted to realize a new motor PWM value (e.g., a second measured motor PWM) defined by the following equation: New Motor PWM=First Measured PWM−(First Motor Current Deviation/50). Conversely, in an exemplary circumstance wherein respirator flow output has decreased, the motor PWM will need to be programmatically increased to increase the respirator output flow. In such an exemplary circumstance, and wherein the first motor speed deviation is determined to be larger than the first motor current deviation, the motor PWM may be programmatically adjusted to realize a new motor PWM value (e.g., a second measured motor PWM) by the following equation: New Motor PWM=First Measured PWM+(First Motor Speed Deviation/ 10). Further, in an exemplary circumstance wherein respirator flow output has decreased and wherein the first motor current deviation is determined to be larger than the first motor speed deviation, the motor PWM may be programmatically adjusted to realize a new motor PWM value (e.g., a second measured motor PWM) defined by the following equation: New Motor PWM=First Measured PWM+(First Motor Current Deviation/50). In various embodiments, the above-described determination of which of the first motor speed deviation and the first motor current deviation comprises a larger value may include comparing the respective absolute values of the first motor speed deviation and the first motor current deviation.

Alternatively, or additionally, the motor PWM may be programmatically adjusted by increasing and/or decreasing the motor PWM by as standardized amount in order to adjust the motor speed of the blower motor. For example, the motor PWM may be increased and/or decreased by a standardized amount such as, for example, at least approximately between one and 10 duty cycle counts (e.g., between one and five duty cycle counts).

With reference again to FIG. 4, upon programmatically adjusting the first measured motor PWM of the blower motor such that blower motor operating parameters of the blower motor define a blower motor operational configuration that corresponds to a respirator output flowrate that is at least substantially consistent with a desired respirator output flowrate, the exemplary method 400 of producing an at least substantially consistent respirator output flowrate may be continued by repeating at least a portion of the operations described herein in reference to Blocks 404-411. For example, as described herein, exemplary method 400 may continue by generating blower motor data comprising, for example, motor voltage data, motor speed data, and motor current data associated with a second instance, wherein the second instance comprises a moment in time that is sequentially after the first instance. As described herein, blower motor data associated with the second instance may be generated by dynamically measuring, for example, a second measured motor PWM, a second measured motor speed, and a second measured motor current (e.g., the motor PWM, motor speed, and motor current measured at the second instance). In various embodiments, at least a portion of the steps of exemplary method 400 described herein in reference to Blocks 404-411 may be repeated at least once (e.g., in perpetuity) in order to ensure that the respirator output flowrate is remains at least substantially consistent over time.

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for operating a blower so as to generate an at least substantially consistent output flowrate, the method comprising:
    programmatically determining an optimized motor speed based at least in part on blower motor data and a blower characterization curve, wherein the blower characterization curve defines a correlation between motor speed and motor voltage of a blower motor configured to generate a desired respirator output flowrate; and
    programmatically adjusting a motor voltage based at least in part on a comparison of measured motor speed data to the optimized motor speed;
    wherein the optimized motor speed comprises the motor speed required for the blower motor to generate the desired output flowrate given a measured motor voltage data;
    wherein the blower characterization curve is defined by one or more blower characterization equations derived based at least in part on a plurality of motor output calibration points.

2. The method of claim 1, wherein at least one of the motor output calibration points corresponds to a respective calibrated operating state defined by a blower production output and the calibrated blower motor configuration wherein the blower motor producing the blower production output and operating at a calibrated motor speed and a calibrated motor voltage is configured to generate the desired respirator output flowrate.

3. The method of claim 1, wherein the plurality of motor output calibration points comprises at least three motor output calibration points such that the blower characterization curve comprises a plurality of blower motor operational ranges, each blower motor operational range being defined by adjacent motor output calibration points of the plurality of motor output calibration points, and wherein each of the one or more blower characterization equations corresponds to a respective blower motor operational range such that the blower characterization curve is defined by a plurality of blower characterization equations.

4. The method of claim 3, further comprising generating the blower motor data comprising the measured motor speed data and the measured motor voltage data, wherein programmatically determining the optimized motor speed comprises identifying a measured blower motor operational range based at least in part on the measured motor voltage data and identifying the blower characterization equation corresponding to measured blower motor operational range.

5. The method of claim 1, wherein the one or more blower characterization equations comprises a derived correlation between the motor speed and the motor voltage of the blower motor configured to generate the desired respirator output flowrate, wherein the derived correlation is based at least in part on the calibrated motor data corresponding to the plurality of motor output calibration points.

6. The method of claim 5, wherein the derived correlation comprises an at least linear correlation.

7. The method of claim 1, further comprising adjusting the measured motor speed based at least in part on measured ambient temperature data.

8. The method of claim 1, further comprising adjusting the measured motor speed based at least in part on measured ambient pressure data.

9. The method of claim 8, further comprising adjusting the measured motor speed based at least in part on measured ambient temperature data.

10. The method of claim 1, further comprising identifying the plurality of motor output calibration points based at least in part on a maximum blower production output of the blower motor.

11. The method of claim 1, wherein programmatically adjusting the motor voltage comprises adjusting a pulse width modulation configuration of the blower motor such that the motor speed of the blower motor is adjusted so as to maintain the respirator output flowrate that is at least substantially consistent with the desired respirator output flowrate.

12. The method of claim 1, further comprising:
programmatically determining an optimized motor current based at least in part on the blower motor data and a second blower characterization curve, wherein the second blower characterization curve defines a correlation between motor current and motor voltage of the blower motor configured to generate the desired respirator output flowrate, wherein the optimized motor current comprises a motor current required for the blower motor to generate the desired respirator output flowrate given the measured motor voltage data; and
programmatically adjusting a motor voltage based at least in part on a comparison of the measured motor current data to the optimized motor current.

13. The method of claim 1, wherein the comparison of the measured motor speed data to the optimized motor speed comprises comparing the measured motor speed to the optimized motor speed in order to determine whether the measured motor speed falls within an acceptable measured motor speed tolerance range defined in part by the optimized motor speed and comprising a range of motor speed values configured to cause the blower motor operating at the measured motor voltage to generate the respirator output flowrate that is at least substantially consistent with the desired respirator output flowrate.

14. A respirator apparatus configured to generate an at least substantially consistent respirator output airflow, the respirator apparatus comprising:
a blower assembly comprising a blower motor configured to control a blower so as to drive a volume of air through a respirator air outlet at a respirator output flowrate; and
a controller comprising at least one processor, and at least one non-transitory memory comprising instructions that, with the at least one processor, cause the controller to:
programmatically determine an optimized motor speed based at least in part on blower motor data and a blower characterization curve, wherein the blower characterization curve defines a correlation between motor speed and motor voltage of the blower motor configured to generate a desired respirator output flowrate; and
programmatically adjust a motor voltage based at least in part on a comparison of a measured motor speed data to the optimized motor speed;
wherein the optimized motor speed comprises the motor speed required for the blower motor to generate the desired output flowrate given a measured motor voltage data;
wherein the blower characterization curve is defined by one or more blower characterization equations derived based at least in part on a plurality of motor output calibration points.

15. The respirator apparatus of claim 14, wherein at least one of the motor output calibration points corresponds to a respective calibrated operating state defined by a blower production output and a calibrated blower motor configuration wherein the blower motor producing the blower production output and operating at a calibrated motor speed and a calibrated motor voltage is configured to generate the desired respirator output flowrate.

16. The respirator apparatus of claim 14, wherein the plurality of motor output calibration points comprises at least three motor output calibration points such that the blower characterization curve comprises a plurality of blower motor operational ranges, each blower motor operational range being defined by adjacent motor output calibration points of the plurality of motor output calibration points, and wherein each of the one or more blower characterization equations corresponds to a respective blower motor operational range such that the blower characterization curve is defined by a plurality of blower characterization equations.

17. The respirator apparatus of claim 16, wherein the at least one non-transitory memory further comprises instructions that, with the at least one processor, cause the apparatus to generate the blower motor data comprising the measured motor speed data and the measured motor voltage data, wherein programmatically determining the optimized motor speed comprises identifying a measured blower motor operational range based at least in part on the measured motor voltage data and identifying the blower characterization equation corresponding to measured blower motor operational range.

18. The respirator apparatus of claim 14, wherein the one or more blower characterization equations comprises a derived correlation between the motor speed and the motor voltage of the blower motor configured to generate the desired respirator output flowrate, wherein the derived correlation is based at least in part on the calibrated motor data corresponding to the plurality of motor output calibration points.

19. The respirator apparatus of claim 14, wherein the at least one non-transitory memory further comprises instructions that, with the at least one processor, cause the apparatus to adjust the measured motor speed based at least in part on measured ambient temperature data.

20. The respirator apparatus of claim 14, wherein the at least one non-transitory memory further comprises instructions that, with the at least one processor, cause the apparatus to adjust the measured motor speed based at least in part on measured ambient pressure data.

* * * * *